(12) United States Patent
Banerian

(10) Patent No.: US 10,137,279 B2
(45) Date of Patent: Nov. 27, 2018

(54) CATHETER GUIDE AND METHOD FOR UTILIZING THE SAME

(71) Applicant: William Beaumont Hospital, Royal Oak, MI (US)

(72) Inventor: Kirk G. Banerian, Bloomfield Hills, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 533 days.

(21) Appl. No.: 14/648,195

(22) PCT Filed: Nov. 27, 2013

(86) PCT No.: PCT/US2013/072247
§ 371 (c)(1),
(2) Date: May 28, 2015

(87) PCT Pub. No.: WO2014/085597
PCT Pub. Date: Jun. 5, 2014

(65) Prior Publication Data
US 2015/0306352 A1    Oct. 29, 2015

Related U.S. Application Data

(60) Provisional application No. 61/731,044, filed on Nov. 29, 2012.

(51) Int. Cl.
*A61M 25/00* (2006.01)
*A61M 25/06* (2006.01)

(52) U.S. Cl.
CPC ....... *A61M 25/0662* (2013.01); *A61M 25/002* (2013.01); *A61M 25/0017* (2013.01); *A61M 25/0097* (2013.01); *A61M 25/0668* (2013.01)

(58) Field of Classification Search
CPC ............ A61M 25/0017; A61M 25/002; A61M 25/0097; A61M 25/0662; A61M 25/0668
See application file for complete search history.

(56) References Cited

U.S. PATENT DOCUMENTS

| 3,861,395 A | 1/1975 | Taniguchi |
| 4,062,363 A * | 12/1977 | Bonner, Jr. ........ A61M 25/0111 604/171 |
| 4,337,775 A | 7/1982 | Cook et al. |
| 4,834,711 A | 5/1989 | Greenfield et al. |

(Continued)

OTHER PUBLICATIONS

International Search Report and Written Opinion for PCT Application PCT/US2013/072247 dated Apr. 28, 2014.

*Primary Examiner* — Kai Weng
(74) *Attorney, Agent, or Firm* — Honigman Miller Schwartz and Cohn LLP; Douglas H. Siegel; Jonathan P. O'Brien

(57) ABSTRACT

An apparatus is disclosed. The apparatus includes a catheter guide (10, 10', 10'', 10''', 10''''). The catheter guide (10, 10', 10'', 10''', 10'''') includes a first conduit (12, 12', 12'', 12''', 12'''') a second conduit (14 14' 14'' 14''' 14'''') and a shield member (16 16' 16'', 16''', 16''''). The second conduit (14, 14', 14'', 14''', 14'''') is connected to an outer surface (26, 26', 26'', 26''', 26'''') of the first conduit (12, 12', 12'', 12''', 12'''').

6 Claims, 16 Drawing Sheets

(56) References Cited

U.S. PATENT DOCUMENTS

| | | |
|---|---|---|
| 5,588,965 A | 12/1996 | Burton et al. |
| 7,022,103 B2 | 4/2006 | Cappiello et al. |
| 2002/0169438 A1 | 11/2002 | Sauer |
| 2003/0114835 A1 | 6/2003 | Noda |
| 2004/0254422 A1 | 12/2004 | Singh |
| 2006/0100607 A1 | 5/2006 | Brown |

* cited by examiner

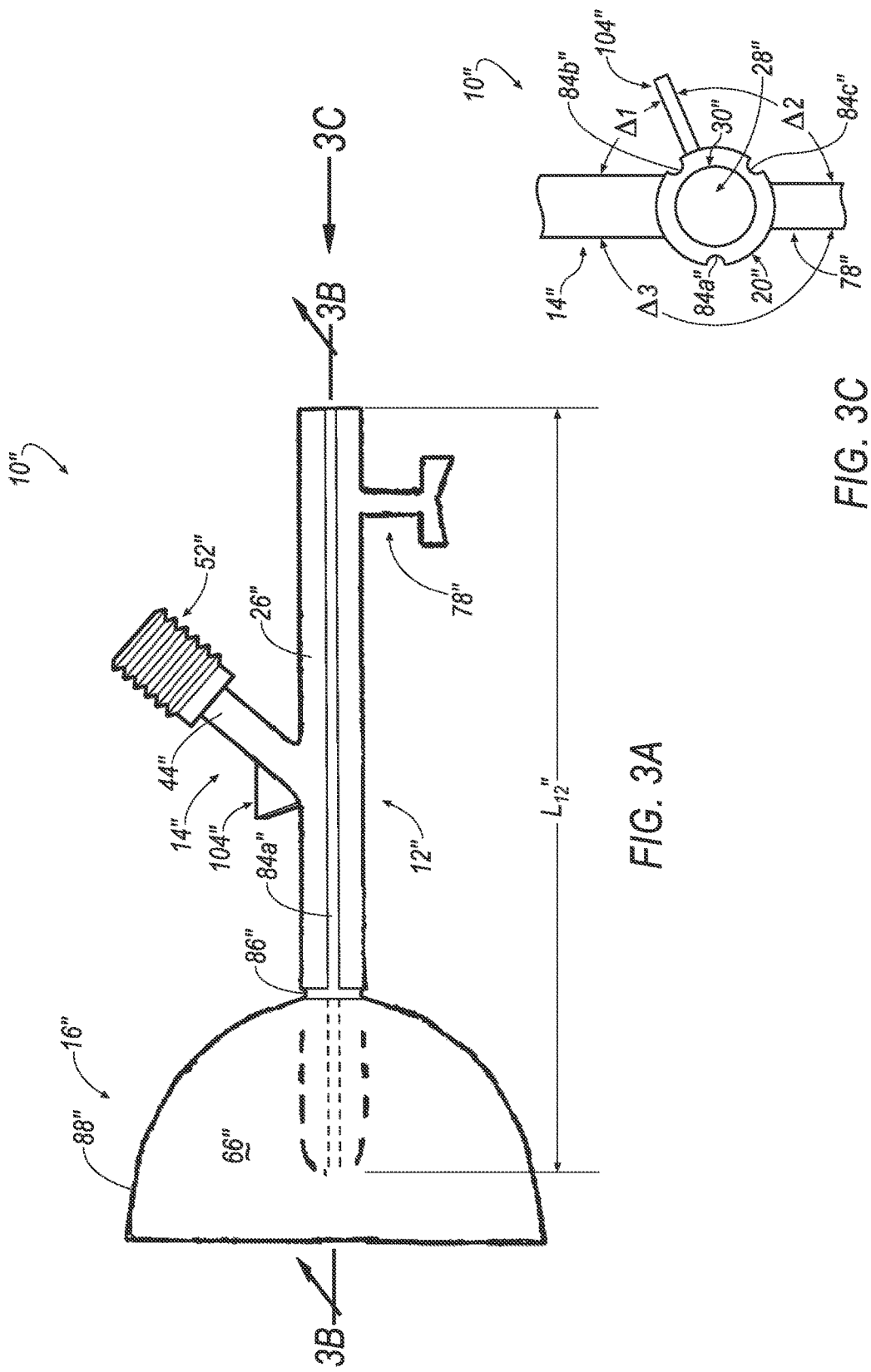

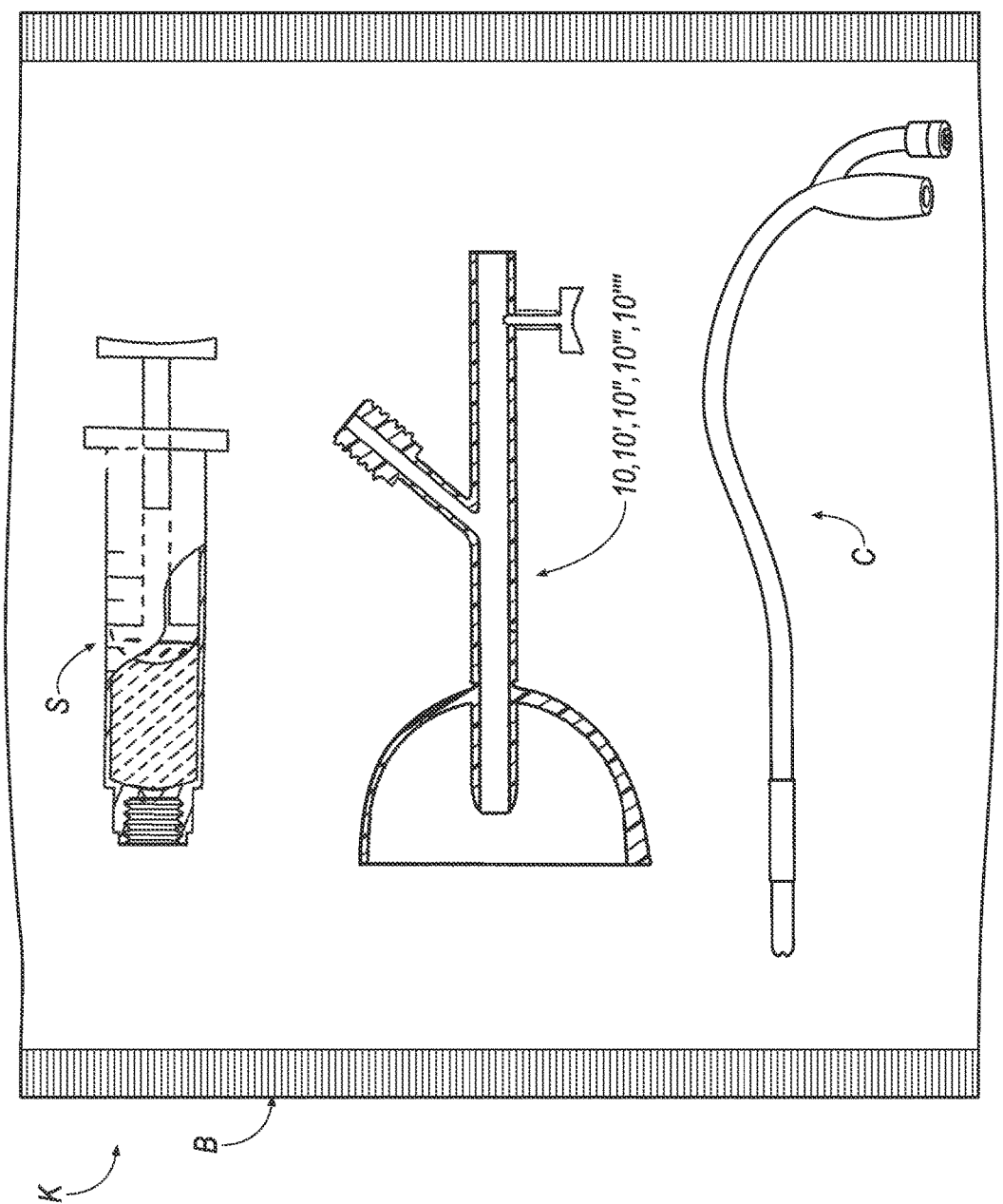

CATHETER GUIDE AND METHOD FOR UTILIZING THE SAME

CROSS-REFERENCE TO RELATED APPLICATIONS

This Patent Application is a 35 U.S.C. § 371 United States National Phase Stage of, and claims priority to, PCT International Application No. PCT/US2013/072247 filed Nov. 27, 2013, which claims the benefit under 35 U.S.C. § 119 of U.S. Provisional Application 61/731,044 filed on Nov. 29, 2012. The entire contents of both of the aforesaid applications are incorporated by reference herein in their entireties.

FIELD OF THE INVENTION

The disclosure relates to a catheter guide and method for utilizing the same.

DESCRIPTION OF THE RELATED ART

Urinary tract catheters are known in the art. Improvements for interfacing a urinary tract catheter with a patient are continuously being sought in order to advance the art.

BRIEF DESCRIPTION OF THE DRAWINGS

The disclosure will now be described, by way of example, with reference to the accompanying drawings, in which:

FIG. 3A is a side view of a catheter guide in accordance with an exemplary embodiment of the invention.

FIG. 3C is an end view of the catheter guide according to arrow 3C of FIG. 3A.

FIG. 7 is a view of an exemplary kit.

SUMMARY

Figure 1A:
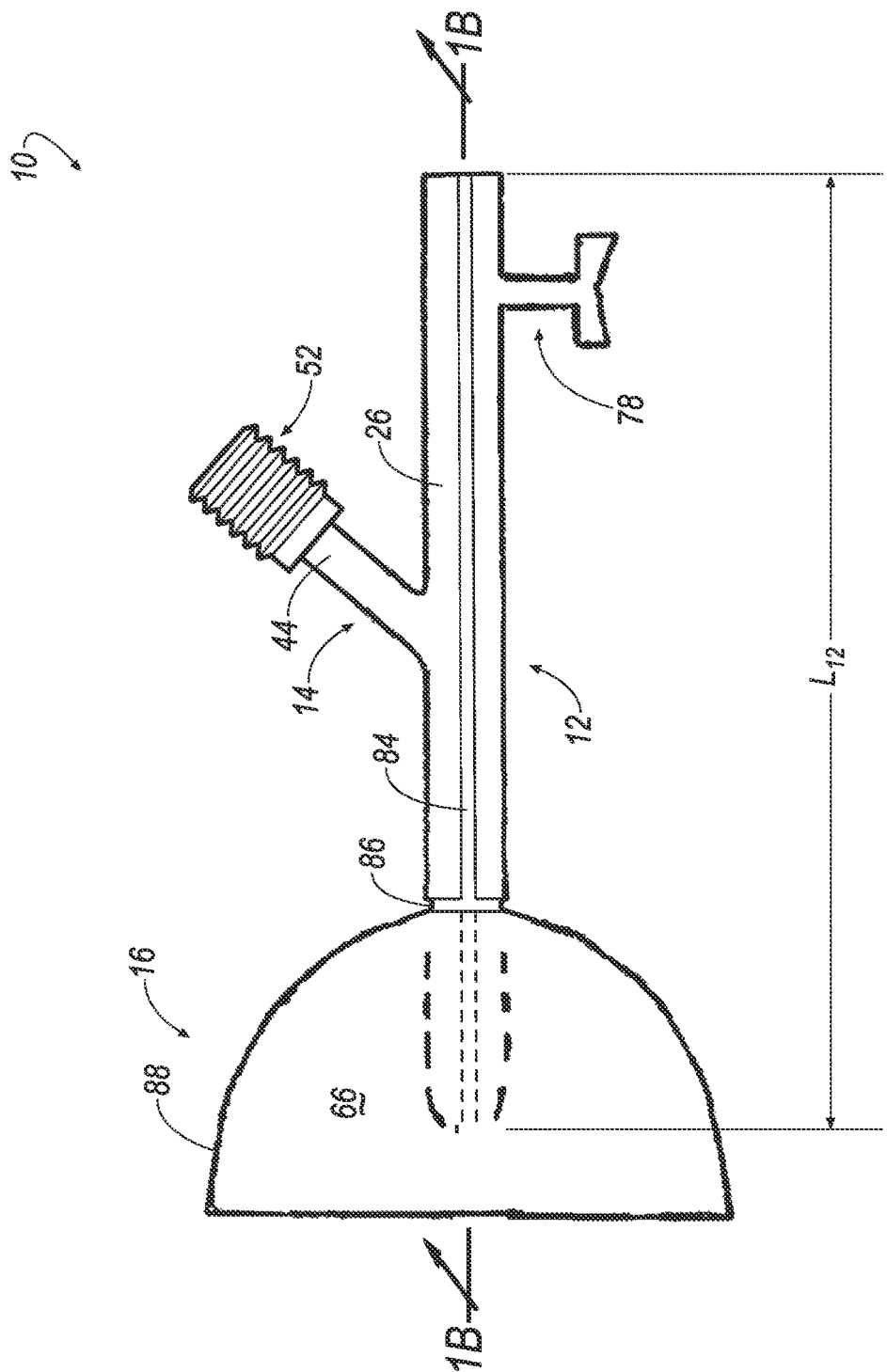
FIG. 1A is a side view of a catheter guide in accordance with an exemplary embodiment of the invention.

One aspect of the disclosure provides an apparatus including a catheter guide. The catheter guide includes a first conduit, a second conduit and a shield member. The second conduit is connected to an outer surface of the first conduit. A passage extending through the first conduit is fluidly-connected to a passage extending through the second conduit. The shield member is connected to the first conduit. The shield member includes an inner surface and an outer surface. The first conduit extends through the shield member such that at least a portion of a length of the first conduit extends beyond the inner surface of the shield member.

In some implementations, the first conduit includes a tube-shaped body having a proximal end, a distal end, an inner surface and the outer surface. The inner surface defines the passage extending through the tube-shaped body from the proximal end to the distal end. Access to the passage is permitted by a proximal opening formed in the proximal end and a distal opening formed in the distal end.

In some examples, the second conduit includes a tube-shaped body having a proximal end, a distal end, an inner surface and an outer surface. The inner surface defines the passage extending through the tube-shaped body from the proximal end to the distal end. Access to the passage is permitted by a proximal opening formed in the proximal end and a distal opening formed in the distal end.

In some instances, a portion of the outer surface of the tube-shaped body near the proximal end of the second conduit includes means for attaching a syringe to the second conduit of the catheter guide.

In some implementations, the tube-shaped body of the second conduit is integrally-formed with and extends from the outer surface of the tube-shaped body of the first conduit.

In some examples, the tube-shaped body of the second conduit extends from the outer surface of the tube-shaped body of the first conduit at a region near between approximately one-quarter to three-quarters of the length of the first conduit.

In some instances, the second conduit is offset from the first conduit by an offset angle. The offset angle is between approximately 45° and 90°.

In some implementations, the shield member includes a bowl-shaped body having a proximal end and a distal end.

In some examples, the bowl-shaped body of the shield member extends from the outer surface of the tube-shaped body of the first conduit at a region near between approximately one-quarter to three quarters of the length of the first conduit and the distal end of the tube-shaped body of the first conduit.

In some instances, the bowl-shaped body circumscribes a portion of the length of the tube-shaped body.

In some implementations, the bowl-shaped body of the shield member is integrally-formed with and extends from the outer surface of the tube-shaped body of the first conduit.

In some examples, the bowl-shaped body of the shield member is separately formed with respect to and is attached to the outer surface of the tube-shaped body of the first conduit by an adapter.

In some instances, the inner surface of the shield member defines a concave side of the shield member whereas the outer surface of the shield member defines a convex side of the shield member. The concave side defines the a glands penis-receiving cavity of the shield member. Access to the glands penis-receiving cavity is permitted by a proximal opening formed in the distal end of the shield member and the distal opening formed in the distal end of the tube-shaped body of the first conduit.

In some implementations, the distal end of the tube-shaped body of the first conduit is arranged within the glands penis-receiving cavity and does not extend beyond the distal end of the bowl-shaped body of the shield member.

In some examples, the distal end of the tube-shaped body of the first conduit is arranged within the glands penis-receiving cavity and extends beyond the distal end of the bowl-shaped body of the shield member.

In some instances, the catheter guide further includes a third conduit connected to the outer surface of the first conduit. The passage extending through the first conduit is fluidly-connected to a passage extending through the third conduit. The third conduit extends from the outer surface of the tube-shaped body of the first conduit at a region near between approximately one-quarter to three-quarters of the length of the first conduit and the proximal end of the tube-shaped body of the first conduit. The third conduit is a fenestration port and the passage extending there-through is a pressure release passageway that permits decompression pressure of the passage extending through the tube-shaped body of the first conduit.

In some implementations, at least the first conduit of the catheter guide includes one or more weakened zones. At least one first weakened zone of the one or more weakened zones longitudinally extends along the length of the first conduit.

In some examples, the catheter guide further includes a grasping member and a third conduit. The grasping member extends radially outwardly from and is integrally connected to the outer surface of the first conduit. The grasping member is angularly offset from the second conduit at a first angle. The third conduit is connected to the outer surface of the first conduit. The passage extending through the first conduit is fluidly-connected to a passage extending through the third conduit. The grasping member is angularly offset from the third conduit at a second angle. The second conduit is angularly offset from the third conduit at a third angle.

In some instances, a first weakened zone of the at least one first weakened zone of the one or more weakened zones longitudinally extends along the length of the first conduit between the second conduit and the grasping member. A second weakened zone of the at least one first weakened zone of the one or more weakened zones longitudinally extends along the length of the first conduit between the grasping member and the third conduit. A third weakened zone of the at least one first weakened zone of the one or more weakened zones longitudinally extends along the length of the first conduit between the second conduit and the third conduit.

In some implementations, at least one second weakened zone of the one or more weakened zones circumferentially extends about an intersection of the first conduit and the shield member at the outer surface of the first conduit where the shield member is connected to the outer surface of the first conduit.

In some examples, at least one second weakened zone of the one or more weakened zones longitudinally extends along the length of the shield member.

In some instances, the catheter guide includes one or more longitudinal seams that longitudinally split the catheter guide into a first part and a second part.

In some implementations, the first part of the catheter guide includes: a first portion of the first conduit, the second conduit and a first portion of the shield member. The second part of the catheter guide includes a second portion of the first conduit and a second portion of the shield member.

In some examples, one or more adapters that selectively-retain the first part of the catheter guide to the second part of the catheter guide.

In some instances, a first adapter of the one or more adapters is a proximal end adapter that is secured to a threaded portion of the outer surface of the first conduit near a proximal end of the first conduit.

In some implementations, the proximal end adapter includes a substantially cylindrical sleeve having a threaded inner surface that cooperates with the threaded portion of the outer surface of the tube-shaped body of the first conduit.

In some examples, the proximal end adapter includes an end body portion that is disposed over a proximal opening formed in the proximal end of the first conduit. The end body portion forms a passage that permits access to the passage extending through the tube-shaped body of the first conduit. The passage of the end body portion is defined by a passage diameter that is substantially equal to or less than the diameter of the passage extending through the first conduit.

In some instances, a second adapter of the one or more adapters is a distal end adapter that is arranged about the outer surface of the first conduit near a region where the shield member is connected to the outer surface of the first conduit.

In some implementations, a first portion of the second conduit is arranged exterior of a glands penis-receiving cavity of the shield member. A second portion of the second conduit extends through a passage formed in the shield member. A third portion of the second conduit is arranged within the glands penis-receiving cavity of the shield member where the second conduit extends from the outer surface of the first conduit.

Another aspect of the disclosure provides a method for utilizing a catheter guide. The method includes the steps of: inserting at least some of a portion of a length of the first conduit into a meatus of the penis; extending at least some of the portion of the length of the first conduit into a urethra of the penis for arranging the passage extending through the first conduit in fluid communication with the urethra of the penis; connecting a syringe including a fluid to the second conduit; arranging a distal end of a catheter within the passage extending through the first conduit for forming a fluid sub-chamber defined by all of the passage extending through the second conduit and a portion of the passage extending through the first conduit; and expelling a portion of the fluid from the syringe into the fluid sub-chamber for guiding the fluid directly into the urethra of the penis for distending the urethra of the penis. The catheter guide includes a first conduit, a second conduit and a shield member. The second conduit is connected to an outer surface of the first conduit. A passage extending through the first conduit is fluidly-connected to a passage extending through the second conduit. The shield member is connected to the first conduit. The shield member is connected to the outer surface of the first conduit. The shield member includes an inner surface and an outer surface. The first conduit extends through the shield member such that at least a portion of a length of the first conduit extends beyond the inner surface of the shield member.

In some implementations, the method further includes the step of: advancing the distal end of a catheter out of the opening formed in the distal end of the first conduit for advancing the distal end of a catheter into the urethra of the penis that is distended by the fluid.

In some examples, the method of claim further includes the steps of: removing the catheter guide from being arranged about the glands penis of the penis while the catheter remains arranged within the passage extending through the first conduit of the catheter guide; and separating the catheter guide into two or more pieces for radially removing the catheter guide from being arranged about the catheter.

In some instances, the separating step includes: longitudinally separating both of the first conduit and the shield member into two or more pieces for radially removing both of the first conduit and the shield member from being arranged about the catheter.

In some implementations, the separating step further includes: firstly circumferentially separating the shield member from the first conduit; and then secondly longitudinally separating the first conduit into two or more pieces for radially removing the first conduit from being arranged about the catheter.

In some examples, the separating step includes: firstly longitudinally separating the shield member into two or more pieces for radially removing the shield member from the first conduit; and then secondly longitudinally separating the first conduit into two or more pieces for radially removing the first conduit from being arranged about the catheter.

In yet another aspect of the disclosure provides a kit. The kit includes a catheter guide and a catheter. The catheter guide includes a first conduit, a second conduit and a shield member. The second conduit is connected to an outer surface of the first conduit. A passage extending through the first conduit is fluidly-connected to a passage extending through the second conduit. The shield member is connected to the first conduit. The shield member is connected to the outer surface of the first conduit. The shield member includes an inner surface and an outer surface. The first conduit extends through the shield member such that at least a portion of a length of the first conduit extends beyond the inner surface of the shield member.

In some implementations, the kit includes a bag containing the catheter guide and the catheter.

In some examples, the kit includes a syringe including fluid. The fluid is a surgical grade fluid, a medical grade viscous lubricating fluid, a disinfectant fluid, a local anesthetic fluid, water or saline.

DETAILED DESCRIPTION OF THE INVENTION

The Figures illustrate exemplary embodiments of a catheter guide and method for utilizing the same. Based on the foregoing, it is to be generally understood that the nomenclature used herein is simply for convenience and the terms used to describe the invention should be given the broadest meaning by one of ordinary skill in the art.

Figure 6A:
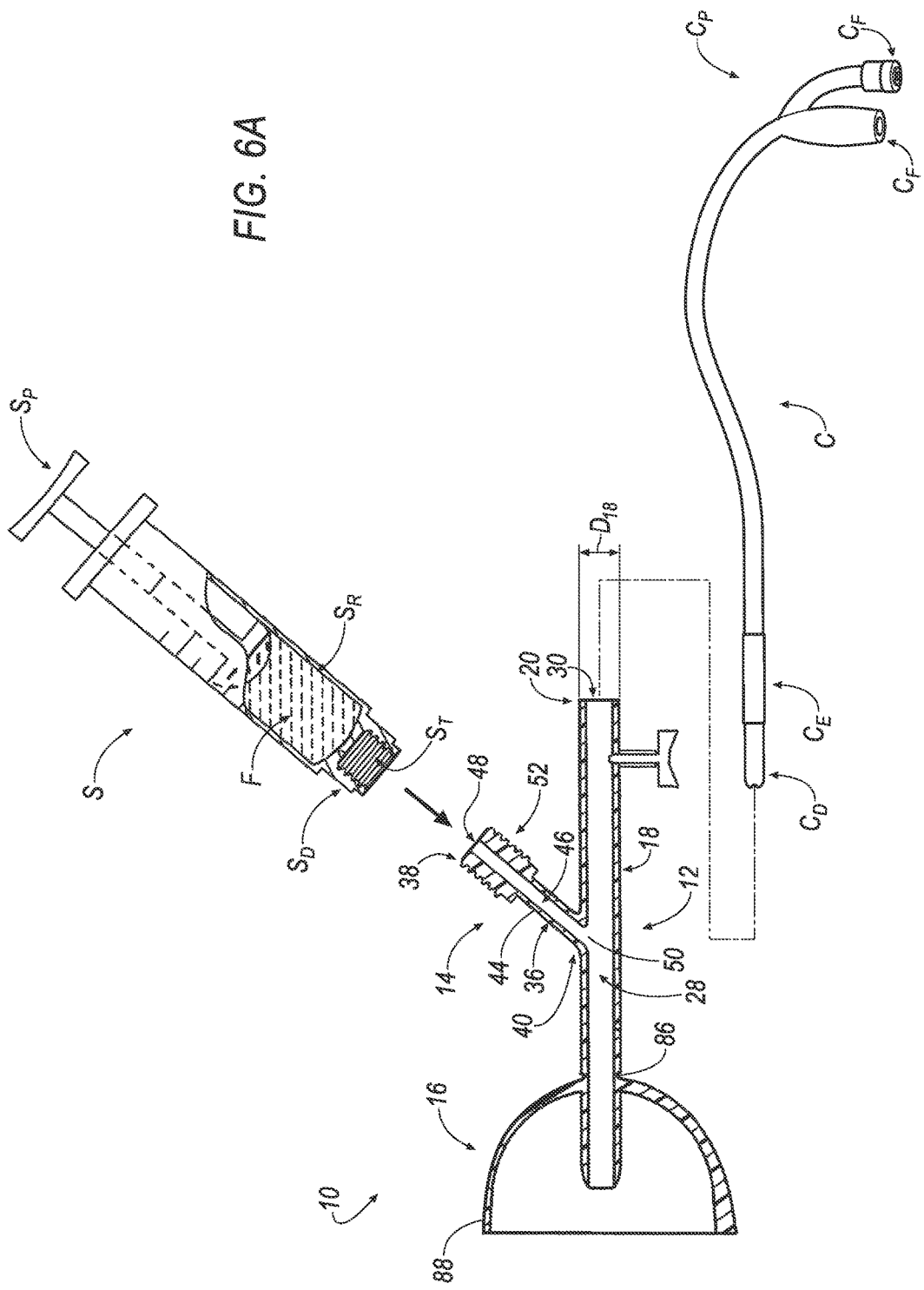
FIGS. 6A-6G are side views of the catheter guide of FIGS. 1A-1B illustrating a method for using the catheter guide.

Referring to FIG. 6A, a urinary tract catheter is shown generally at C. In some implementations, the urinary tract catheter, C, may be a Foley catheter. Foley catheters, C, include a distal end, $C_D$, including an expandable member, $C_E$. Foley catheters, C, also include a proximal end, $C_P$, including one or more fluid interface ports, $C_F$, that may be fluidly-connected to, for example, a urine collection bag (not shown); if, for example, two fluid interface ports, $C_F$, are arranged at the proximal end, $C_P$, of the catheter, C, the proximal end, $C_P$, of the catheter, C, may include a "Y" configuration. The expandable member, $C_E$, near the distal end, $C_D$, of the catheter, C, is intended to be placed within a urinary bladder (now shown) of a patient; when located within the urinary bladder and arranged in an inflated orientation, the expandable member, $C_E$, prevents the distal end, $C_D$, of the catheter, C, from being withdrawn out of the urinary bladder. Functionally, the catheter, C, transports urine from the urinary bladder to the urine collection bag.

Figure 4:
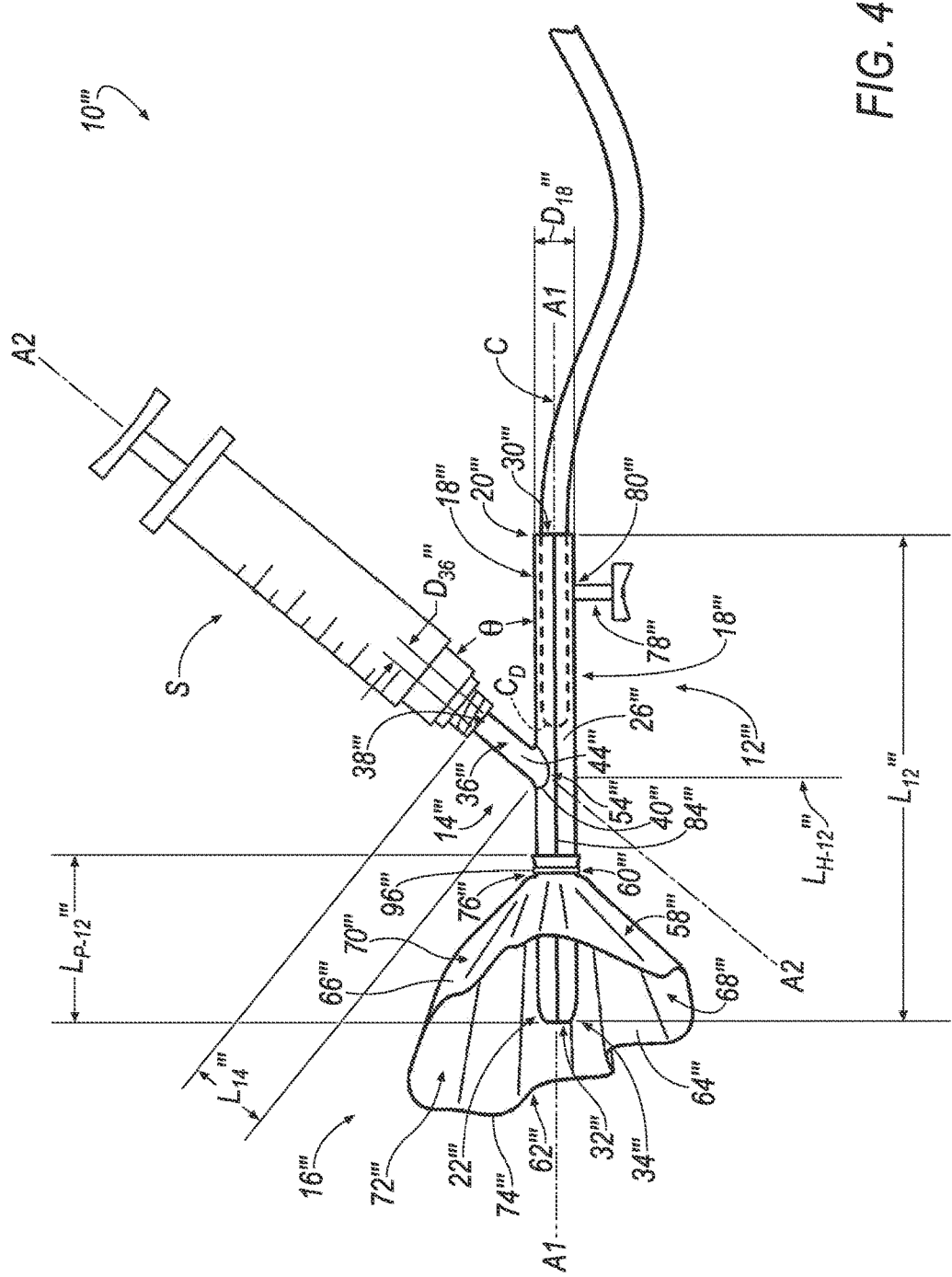
FIG. 4 is a side view of a catheter guide in accordance with an exemplary embodiment of the invention.
Figure 5:
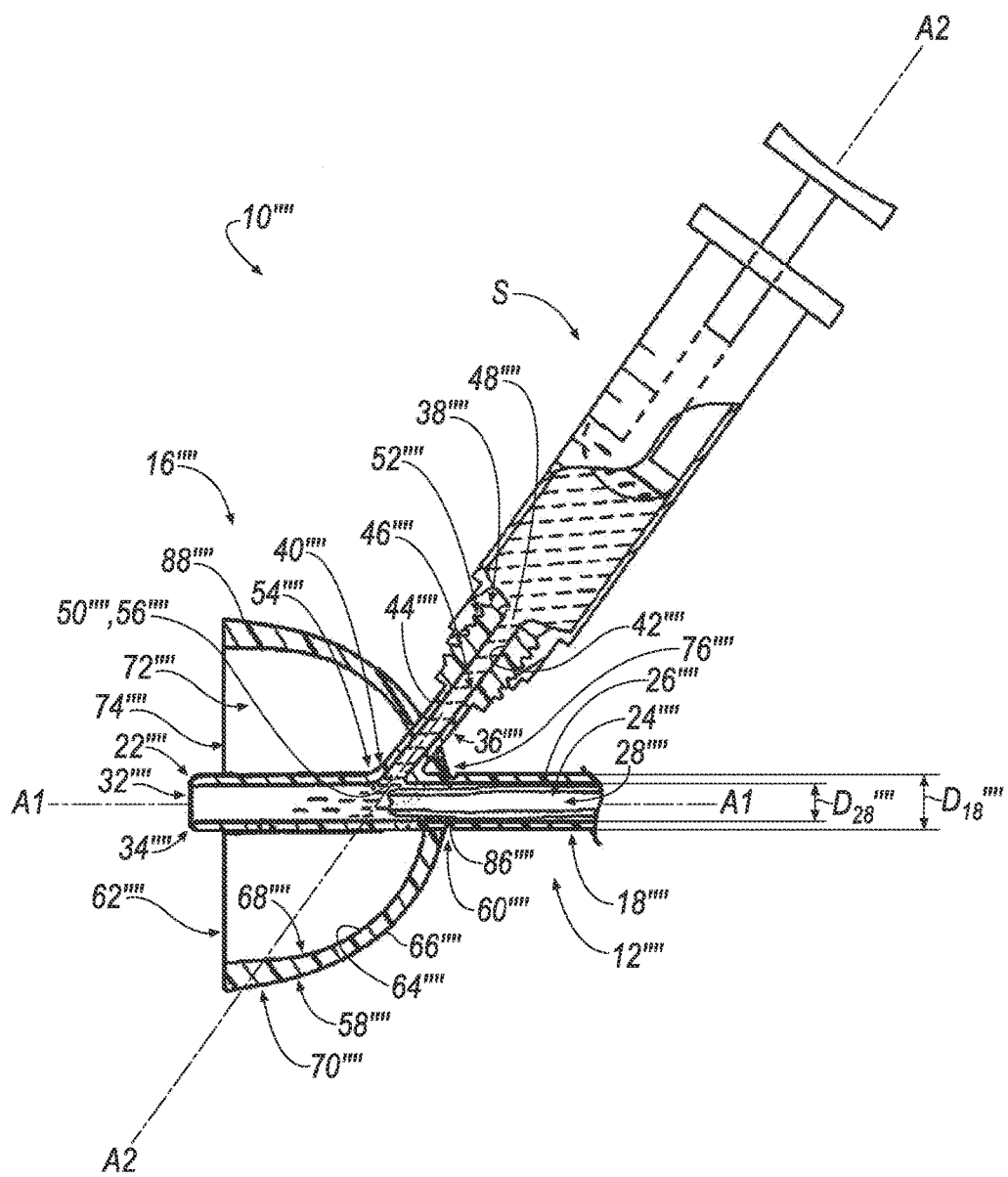
FIG. 5 is a side view of a catheter guide in accordance with an exemplary embodiment of the invention.

The distal end, $C_D$, of the catheter, C, may be guided toward the urinary bladder of the patient with the assistance of a catheter guide 10 (see, e.g., FIGS. 1A-1B), 10' (see, e.g., FIGS. 2A-2B), 10" (see, e.g., FIGS. 3A-3B), 10'" (see, e.g., FIG. 4), 10"" (see, e.g., FIG. 5). As will be described in the following disclosure, the catheter guide 10, 10', 10", 10'", 10"" includes structure that interfaces with a body member, P (see, e.g., FIGS. 6B-6G), of a patient. In some implementations, the body member, P, of the patient is a penis.

For purposes of referencing how the catheter guide 10, 10', 10", 10'", 10"" interfaces with the penis, P, the following description of the anatomy of the penis, P, is provided. With reference to FIGS. 6B-6G, the urinary bladder is in fluid communication with a fluid evacuation conduit, $P_C$, extending through the penis, P; the fluid evacuation conduit, $P_C$, is called the urethra. The fluid evacuation conduit, $P_C$, terminates at a distal end, $P_D$, of the penis, P; the distal end, $P_D$, of the penis, P, is called the glands penis. An opening, $P_O$, is formed in the glands penis, $P_D$, and is in fluid communication with urethra, $P_C$; the opening, $P_O$, is called the meatus. The meatus, $P_O$, is the location of the penis, P, where urine is evacuated from the body of patient.

Figure 1B:
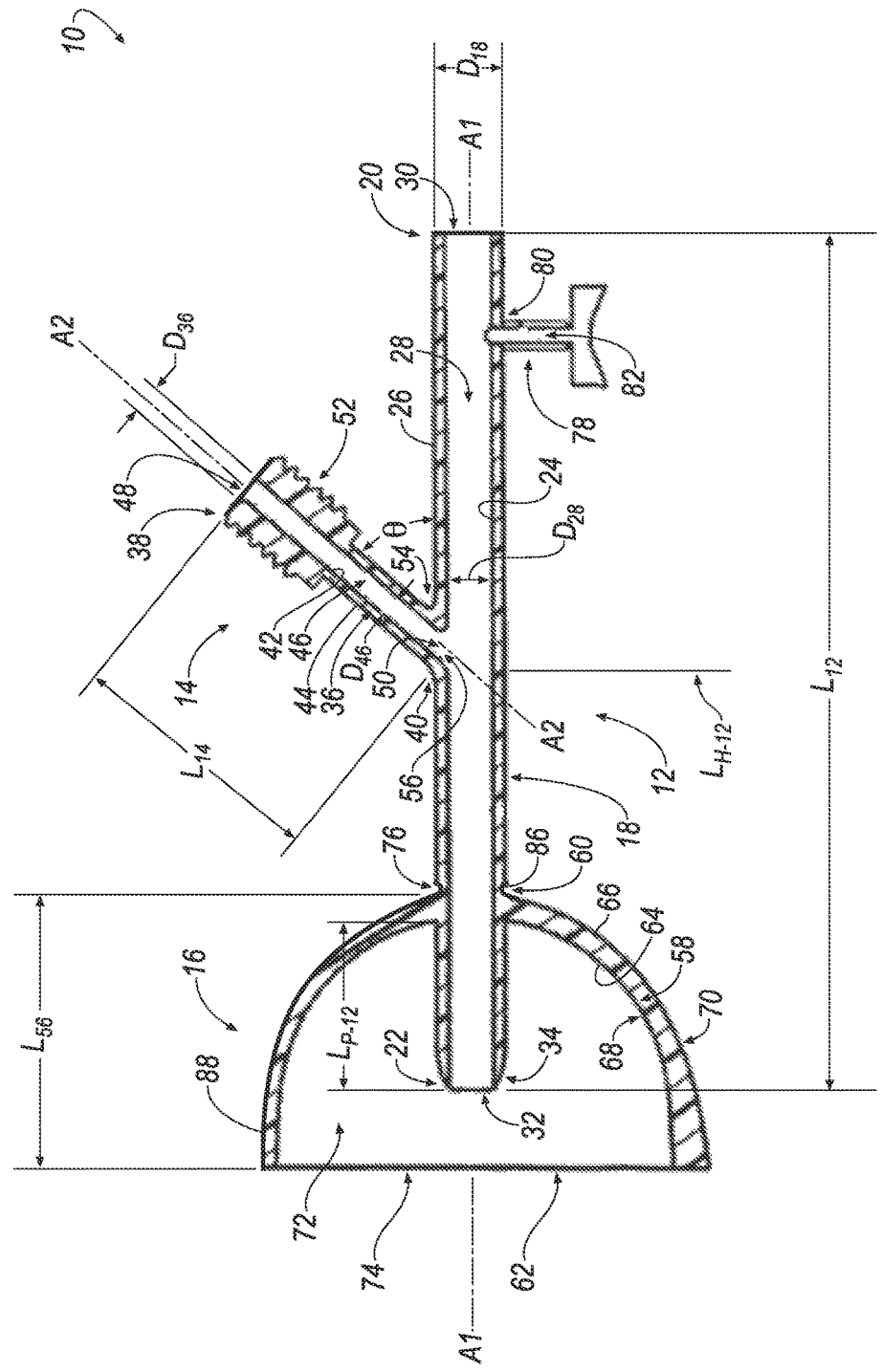
FIG. 1B is a cross-sectional view according to line 1B-1B of FIG. 1A.

Referring now to the FIGS. 1A-1B, an exemplary catheter guide is shown generally at 10. The catheter guide 10 includes a first conduit 12, a second conduit 14 and a shield member 16. The second conduit 14 is connected to the first conduit 12. The shield member 16 is connected to the first conduit 12.

Referring to FIG. 1B, the first conduit 12 includes a tube-shaped body 18 having a proximal end 20, a distal end 22, an inner surface 24 and an outer surface 26. The inner surface 24 defines a passage 28 extending through the tube-shaped body 18 from the proximal end 20 to the distal end 22. Access to the passage 28 is permitted by a proximal opening 30 formed in the proximal end 20 and a distal opening 32 formed in the distal end 22. As will be described in the following disclosure at FIGS. 6A-6G, the passage 28 may contain one or more of the catheter, C, and a fluid, F, from a syringe, S; therefore, the passage 28 may be alternatively referred to as a catheter-and-fluid-receiving passage.

The inner surface 24 may define the passage 28 to include a substantially constant passage diameter, $D_{28}$, that extends along an entire length, $L_{12}$, of the first conduit 12. The outer surface 26 may define the tube-shaped body 18 to include a substantially constant outer diameter, $D_{18}$, along the entire length, $L_{12}$, of the first conduit 12; however, in some implementations, a portion of the outer surface 26 of the tube-shaped body 18 near, for example, the distal end 22 of the first conduit 12 may include a subtly progressively-reduced outer diameter, $D_{18}$, thereby defining the tube-shaped body 18 to include a conical, tapered distal end portion 34; the tapered distal end portion 34 may assist in axially aligning the distal end 22 of the first conduit 12 into the meatus, $P_O$, of the penis, P.

The second conduit 14 includes a tube-shaped body 36 having a proximal end 38, a distal end 40, an inner surface 42 and an outer surface 44. The inner surface 42 defines a passage 46 extending through the tube-shaped body 36 from the proximal end 38 to the distal end 40. Access to the passage 46 is permitted by a proximal opening 48 formed in the proximal end 38 and a distal opening 50 formed in the distal end 40. As will be described in the following disclosure at FIGS. 6A-6G, the passage 46 may permit passage of a fluid, F, from a syringe, S; therefore, the passage 46 may be alternatively referred to as a fluid-propagating passage.

The inner surface 42 may define the passage 46 to include a substantially constant passage diameter, $D_{46}$, along an entire length, $L_{14}$, of the second conduit 14. The outer surface 44 may define the tube-shaped body 36 to include a substantially constant outer diameter, $D_{36}$, along the entire length, $L_{14}$, of the second conduit 14; however, in some implementations, a portion of the outer surface 44 of the tube-shaped body 36 near the proximal end 38 of the second conduit 14 may include an increased outer diameter, $D_{36}$, having a threaded surface portion 52. As will be discussed in the following disclosure at FIGS. 6A-6B, the threaded surface portion 52 permits attachment of a fluid container (e.g., a syringe, S) to the second conduit 14 of the catheter guide 10. Although the portion of the outer surface 44 of the tube-shaped body 36 near the proximal end 38 of the second conduit 14 includes a threaded surface portion 52 for facilitating connection of a fluid container to the second conduit 14 of the catheter guide 10, the structure defining the tube-shaped body 36 near the proximal end 38 of the second conduit 14 may include other structure, such as, for example, a cone-shaped male-female coupling, a Luer lock or the like for facilitating attachment of fluid container (e.g., a syringe, F) to the second conduit 14 of the catheter guide 10.

The tube-shaped body 36 of the second conduit 14 is integrally-formed with and extends from the outer surface 26 of the tube-shaped body 18 of the first conduit 12. In some examples, the tube-shaped body 36 of the second conduit 14 extends from the outer surface 26 of the tube-shaped body 18 of the first conduit 12 at a region 54 near between approximately one-quarters to three-quarters (e.g., half, $L_{H-12}$) of the length, $L_{12}$, of the first conduit 12. In some instances, the second conduit 14 is offset from the first conduit 12 by an offset angle, θ (which may be between approximately 45° and 90°), which is referenced from a first axis, A1-A1, that extends through an axial center of the passage 28 of the first conduit 12, and, a second axis, A2-A2, that extends through an axial center of the passage 46 of the second conduit 14.

The passage 28 extending through the first conduit 12 is fluidly-connected to the passage 46 extending through the second conduit 14. In some instances, the passage 28 is fluidly-connected to the passage 46 by way of a radial passage 56 formed in the first conduit 12 near the region 54 that is located near the middle of the length, $L_{12}$, of the first conduit 12. In some examples, the radial passage 56 formed in the first conduit 12 may also be the distal opening 50 formed in the distal end 40 of the tube-shaped body 36 of the second conduit 14.

The shield member 16 includes a bowl-shaped body 58 having a proximal end 60, a distal end 62, an inner surface 64 and an outer surface 66. The first axis, A1-A1, extending through the axial center of the passage 28 of the first conduit 12 also extends through an axial center of the bowl-shaped body 58. The inner surface 64 of the shield member 16 defines a concave side 68 of the shield member 16 whereas the outer surface 66 of the shield member 16 defines a convex side 70 of the shield member 16. The concave side 68 defines the shield member 16 to include a glands penis-receiving cavity 72. Access to the glands penis-receiving cavity 72 is permitted by a proximal opening 74 formed in the distal end 62 of the shield member 16 and the distal opening 32 formed in the distal end 22 of the tube-shaped body 18 of the first conduit 12.

The bowl-shaped body 58 of the shield member 16 is integrally-formed with and extends from the outer surface 26 of the tube-shaped body 18 of the first conduit 12. In some examples, the bowl-shaped body 58 of the shield member 16 extends from the outer surface 26 of the tube-shaped body 18 of the first conduit 12 at a region 76 near between approximately one-quarter to three-quarters (e.g., half, $L_{H-12}$) of the length, $L_{12}$, of the first conduit 12 and the distal end 22 of the tube-shaped body 18 of the first conduit 12. In some instances, the bowl-shaped body 58 circumscribes a portion, $L_{P-12}$, of the length, $L_{12}$, of the tube-shaped body 18. In some examples, the distal end 22 of the tube-shaped body 18 is arranged within the glands penis-receiving cavity 72 and does not extend beyond the distal end 62 of the bowl-shaped body 58 of the shield member 16.

Although some implementations of the shield member 16 may include bowl-shaped body 58 having an inner surface 64 and an outer surface 66 that defines, respectively, a concave side 68 and a convex side 70, the shield member 16 is not limited to by a particular geometry. For example, the shield member may include an inner surface and an outer surface that may extend from and be arranged substantially perpendicularly with respect to the outer surface 26 of the tube-shaped body 18 of the first conduit 12. Accordingly, in such an exemplary implementation, the inner surface may not form a glands penis-receiving cavity 72 but, rather, defines a stop surface for limiting insertion of the length, $L_{12}$, of the tube-shaped body 18 of the first conduit 12 to be approximately equal to the portion, $L_{P-12}$, of the length, $L_{12}$, of the tube-shaped body 18 of the first conduit 12.

In some implementations, the catheter guide 10 includes a third conduit 78 that is integrally-formed with and extends from the outer surface 26 of the tube-shaped body 18 of the first conduit 12. In some examples, the third conduit 78 extends from the outer surface 26 of the tube-shaped body 18 of the first conduit 12 at a region 80 near between approximately one-quarter to three-quarters (e.g., half, $L_{H-12}$) of the length, $L_{12}$, of the first conduit 12 and the proximal end 20 of the tube-shaped body 18 of the first conduit 12.

The third conduit 78 may be referred to as a fenestration port, which defines a pressure release passageway 82 that is in fluid communication with the passage 28 extending through the tube-shaped body 18 of the first conduit 12. Functionally, the fenestration port 78 permits a desired decompression pressure of the passage 28 extending through the tube-shaped body 18 of the first conduit 12. In some instances, a selectively-designed diameter of the pressure release passageway 82 of the fenestration port 78 permits omission of a valve element in the design of the fenestration port 78. Although the fenestration port 78 is shown extending from and arranged in fluid communication with the first conduit 12, the fenestration port 78 may be alternatively arranged in a manner extending from and being in fluid communication with the passage 46 of the second conduit 14.

The catheter guide 10 also includes one or more weakened zones 84, 86, 88. If the one or more weakened zones 84, 86, 88 is/are provided on the inner surface 24, 42, 64 of the first and second conduits 12, 14 and/or the shield member 16, the one or more weakened zones 84, 86, 88 may also assist in the function of the fenestration port 78 described above.

Referring to FIG. 1A, in some implementations, the weakened zone 84 may be arranged along the length, $L_{12}$, of the tube-shaped body 18 of the first conduit 12. The weakened zone 84 may be a recess, groove, slot or valley that is formed in one or both of the inner surface 24 and the outer surface 26 of the tube-shaped body 18 of the first conduit 12.

Referring to FIGS. 1A-1B, in some implementations, the weakened zone 86 may be circumferentially arranged about the intersection of the tube-shaped body 18 of the first conduit 12 and the bowl-shaped body 56 of the shield member 16 near the region 76. The weakened zone 86 may be a recess, groove, slot or valley that is formed in one or more of the inner surfaces 24, 64 and the outer surfaces 26, 66 of the tube-shaped body 18 of the first conduit 12 and the bowl-shaped body 58 of the shield member 16.

Referring to FIGS. 1A-1B, in some implementations, the weakened zone 88 may be arranged along a length, $L_{56}$, of the bowl-shaped body 56 of the shield member 16. The weakened zone 88 may be a recess, groove, slot or valley that is formed in one or both of the inner surface 64 and the outer surface 66 of the bowl-shaped body 56 of the shield member 16.

As will be described in the following disclosure at FIG. 6G, the one or more weakened zones 84, 86, 88 permit removal of the catheter guide 10 from about the catheter, C, and the penis, P, once the distal end, $C_D$, of the catheter, C, is arranged within the urinary bladder of the patient. Functionally, the one or more weakened zones 84, 86, 88 may permit one or more of the first conduit 12 and the shield member 16 to be frangible such that, for example: (1) as seen in FIG. 6G, the first conduit 12 may be split apart along the length, $L_{12}$, of the first conduit 12 as a result of the inclusion of the weakened zone 84, (2) as seen in FIG. 6G, the first conduit 12 may be separated from the shield member 16 as a result of the inclusion of the weakened zone 86, and (3) as seen in FIG. 6G, the shield member 16 may be split apart along the length, $L_{56}$, of the shield member 16 as a result of the inclusion of the weakened zone 88.

Figure 2A:
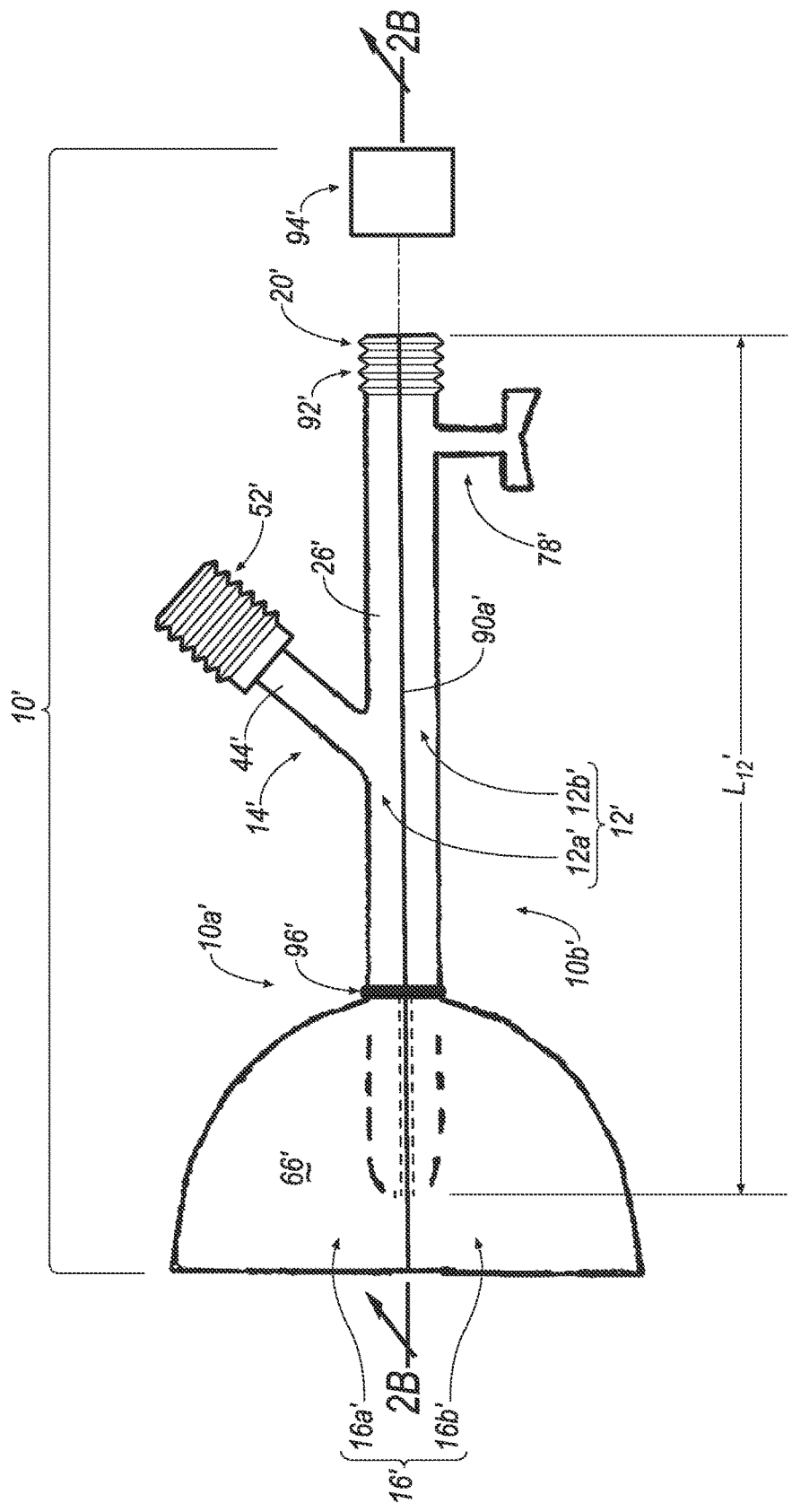
FIG. 2A is a side view of a catheter guide in accordance with an exemplary embodiment of the invention.
Figure 2B:
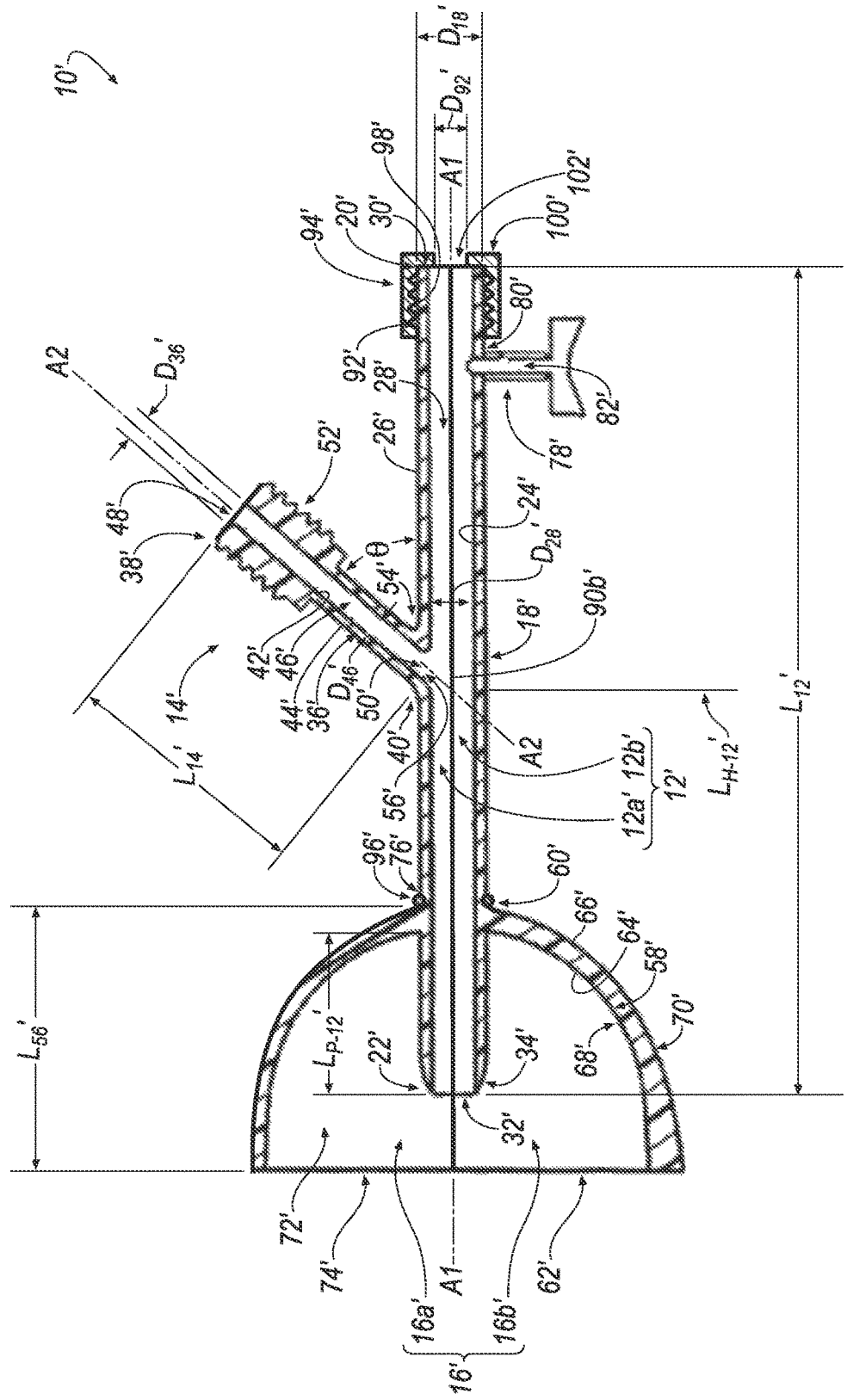
FIG. 2B is a cross-sectional view according to line 2B-2B of FIG. 2A.

Referring now to the FIGS. 2A-2B, an exemplary catheter guide is shown generally at 10'. The catheter guide 10' includes a first conduit 12', a second conduit 14' and a shield member 16'. The second conduit 14' is connected to the first conduit 12'. The shield member 16' is connected to the first conduit 12'.

The first conduit 12' includes a tube-shaped body 18' having a proximal end 20', a distal end 22', an inner surface 24' and an outer surface 26'. The inner surface 24' defines a passage 28' extending through the tube-shaped body 18' from the proximal end 20' to the distal end 22'. Access to the passage 28' is permitted by a proximal opening 30' formed in the proximal end 20' and a distal opening 32' formed in the distal end 22'. As will be described in the following disclosure at FIGS. 6A-6G, the passage 28' may contain one or more of the catheter, C, and a fluid, F, from a syringe, S; therefore, the passage 28' may be alternatively referred to as a catheter-and-fluid-receiving passage.

The inner surface 24' may define the passage 28' to include a substantially constant passage diameter, $D_{28}'$, that extends along an entire length, $L_{12}'$, of the first conduit 12'. The outer surface 26' may define the tube-shaped body 18' to include a substantially constant outer diameter, $D_{18}'$, along the entire length, $L_{12}'$, of the first conduit 12'; however, in some implementations, a portion of the outer surface 26' of the tube-shaped body 18' near, for example, the distal end 22' of the first conduit 12' may include a subtly progressively-reduced outer diameter, $D_{18}'$, thereby defining the tube-shaped body 18' to include a conical, tapered distal end portion 34'; the tapered distal end portion 34' may assist in axially aligning the distal end 22' of the first conduit 12' into the meatus, $P_O$, of the penis, P'.

The second conduit 14' includes a tube-shaped body 36' having a proximal end 38', a distal end 40', an inner surface 42' and an outer surface 44'. The inner surface 42' defines a passage 46' extending through the tube-shaped body 36' from the proximal end 38' to the distal end 40'. Access to the passage 46' is permitted by a proximal opening 48' formed in the proximal end 38' and a distal opening 50' formed in the distal end 40'. As will be described in the following disclosure at FIGS. 6A-6G, the passage 46' may permit passage of a fluid, F, from a syringe, S; therefore, the passage 46' may be alternatively referred to as a fluid-propagating passage.

The inner surface 42' may define the passage 46' to include a substantially constant passage diameter, $D_{46}'$, along an entire length, $L_{14}'$, of the second conduit 14'. The outer surface 44' may define the tube-shaped body 36' to include a substantially constant outer diameter, $D_{36}'$, along the entire length, $L_{14}'$, of the second conduit 14'; however, in some implementations, a portion of the outer surface 44' of the tube-shaped body 36' near the proximal end 38' of the second conduit 14' may include an increased outer diameter, $D_{36}'$, having a threaded surface portion 52'. As will be discussed in the following disclosure at FIGS. 6A-6B, the threaded surface portion 52 permits attachment of a fluid container (e.g., a syringe, F) to the second conduit 14 of the catheter guide 10. Although the portion of the outer surface 44 of the tube-shaped body 36 near the proximal end 38 of the second conduit 14 includes a threaded surface portion 52 for facilitating connection of a fluid container to the second conduit 14 of the catheter guide 10, the structure defining the tube-shaped body 36 near the proximal end 38 of the second conduit 14 may include other structure, such as, for example, a cone-shaped male-female coupling, a Luer lock or the like for facilitating attachment of fluid container (e.g., a syringe, F) to the second conduit 14 of the catheter guide 10.

The tube-shaped body 36' of the second conduit 14' is integrally-formed with and extends from the outer surface 26' of the tube-shaped body 18' of the first conduit 12'. In some examples, the tube-shaped body 36' of the second conduit 14' extends from the outer surface 26' of the tube-shaped body 18' of the first conduit 12' at a region 54' near between approximately one-quarter to three-quarters (e.g., half, $L_{H-12}'$) of the length, $L_{12}'$, of the first conduit 12'. In some instances, the second conduit 14' is offset from the first conduit 12' by an offset angle, θ (which may be between approximately 45° and 90°), which is referenced from a first axis, A1-A1, that extends through an axial center of the passage 28' of the first conduit 12', and, a second axis, A2-A2, that extends through an axial center of the passage 46' of the second conduit 14'.

The passage 28' extending through the first conduit 12' is fluidly-connected to the passage 46' extending through the second conduit 14'. In some instances, the passage 28' is fluidly-connected to the passage 46' by way of a radial passage 56' formed in the first conduit 12' near the region 54' that is located near the middle of the length, $L_{12}'$, of the first conduit 12'. In some examples, the radial passage 56' formed in the first conduit 12' may also be the distal opening 50' formed in the distal end 40' of the tube-shaped body 36' of the second conduit 14'.

The shield member 16' includes a bowl-shaped body 58' having a proximal end 60', a distal end 62', an inner surface 64' and an outer surface 66'. The first axis, A1-A1, extending through the axial center of the passage 28' of the first conduit 12' also extends through an axial center of the bowl-shaped body 58'. The inner surface 64' of the shield member 16' defines a concave side 68' of the shield member 16' whereas the outer surface 66' of the shield member 16' defines a convex side 70' of the shield member 16'. The concave side 68' defines the shield member 16' to include a glands penis-receiving cavity 72'. Access to the glands penis-receiving cavity 72' is permitted by a proximal opening 74' formed in the distal end 62' of the shield member 16' and the distal opening 32' formed in the distal end 22' of the tube-shaped body 18' of the first conduit 12'.

The bowl-shaped body 58' of the shield member 16' is integrally-formed with and extends from the outer surface 26' of the tube-shaped body 18' of the first conduit 12'. In some examples, the bowl-shaped body 58' of the shield member 16' extends from the outer surface 26' of the tube-shaped body 18' of the first conduit 12' at a region 76' near between approximately one-quarters to three-quarters (e.g., half, $L_{H-12}'$) of the length, $L_{12}'$, of the first conduit 12' and the distal end 22' of the tube-shaped body 18' of the first conduit 12'. In some instances, the bowl-shaped body 58' circumscribes a portion, $L_{P\text{-}12}'$, of the length, $L_{12}'$, of the tube-shaped body 18'. In some examples, the distal end 22' of the tube-shaped body 18' is arranged within the glands penis-receiving cavity 72' and does not extend beyond the distal end 62' of the bowl-shaped body 58' of the shield member 16'.

Although some implementations of the shield member 16' may include bowl-shaped body 58' having an inner surface 64' and an outer surface 66' that defines, respectively, a concave side 68' and a convex side 70', the shield member 16' is not limited to a particular geometry. For example, the shield member 16' may include an inner surface and an outer surface that may extend from and be arranged substantially perpendicularly with respect to the outer surface 26' of the tube-shaped body 18' of the first conduit 12'. Accordingly, in such an exemplary implementation, the inner surface may not glands penis-receiving cavity 72' but, rather, define a stop surface for limiting insertion of the length, $L_{12}'$, of the tube-shaped body 18' of the first conduit 12' to be approximately equal to the portion, $L_{P\text{-}12}'$, of the length, $L_{12}'$, of the tube-shaped body 18' of the first conduit 12'.

In some implementations, the catheter guide 10' includes a third conduit 78' that is integrally-formed with and extends from the outer surface 26' of the tube-shaped body 18' of the first conduit 12'. In some examples, the third conduit 78' extends from the outer surface 26' of the tube-shaped body 18' of the first conduit 12' at a region 80' near between approximately one-quarter to three quarters (e.g., half, $L_{H\text{-}12}'$) of the length, $L_{12}'$, of the first conduit 12' and the proximal end 20' of the tube-shaped body 18' of the first conduit 12'.

The third conduit 78' may be referred to as a fenestration port, which defines a pressure release passageway 82' that is in fluid communication with the passage 28' extending through the tube-shaped body 36' of the first conduit 12'. Functionally, the fenestration port 78' permits a desired decompression pressure of the passage 28' extending through the tube-shaped body 18 of the first conduit 12'. In some instances, a selectively-designed diameter of the pressure release passageway 82' of the fenestration port 78' permits omission of a valve element in the design of the fenestration port 78'. Although the fenestration port 78' is shown extending from and arranged in fluid communication with the first conduit 12', the fenestration port 78' may be alternatively arranged in a manner extending from and being in fluid communication with the passage 46' of the second conduit 14'.

The catheter guide 10' also includes one or more weakened zones (see, e.g., 84, 86, 88), which may function in a substantially similar manner as described above in FIGS. 1A-1B. However, in some implementations, the catheter guide 10' may not include one or more weakened zones but rather alternatively include one or more seams 90a' (see, e.g., FIG. 2A), 90b' (see, e.g., FIG. 2B). The seams 90a', 90b' may longitudinally split the catheter guide 10' into a first part 10a' and a second part 10b'. The seams 90a', 90b' may be aligned with the axis A1-A1. The first part 10a' of the catheter guide 10' forms a first portion 12a' of the first conduit 12', the second conduit 14' and a first portion 16a' of the shield member 16'. The second part 10b' of the catheter guide 10' includes a second portion 12b' of the first conduit 12' and a second portion 16b' of the shield member 16'. The first portion 16a' of the shield 16' and the second conduit 14' may be integrally connected to the first portion 12a' of the first conduit 12'. The second portion 16b' of the shield member 16' may be integrally connected to the second portion 12b' of the first conduit 12'.

Because the seam 90a', 90b' splits the catheter guide 10' into the first part 10a' and the second part 10b', one or more adapters 94', 96' may be utilized for selectively-retaining the first part 10a' of the catheter guide 10' to the second part 10b' of the catheter guide 10'. The adapter 94' may be referred to as a proximal end adapter that is secured to a threaded portion 92' of the outer surface 26' of the tube-shaped body 18' of the first conduit 12' near the proximal end 20' of the tube-shaped body 18'. The adapter 96' may be referred to as a distal end adapter that is arranged about a region 76' near between approximately one-quarter to three-quarters (e.g., half, $L_{H\text{-}12}'$) of the length, $L_{12}'$, of the first conduit 12' and the distal end 22' of the tube-shaped body 18' of the first conduit 12'. In some implementations, the distal end adapter 96' may be an elastic band.

Referring to FIG. 2B, the proximal end adapter 94' may include a substantially cylindrical sleeve having a threaded inner surface 98' that cooperates with the threaded portion 92' of the outer surface 26' of the tube-shaped body 18' of the first conduit 12'. The proximal end adapter 94' may also include an end body portion 100' that is disposed over the proximal opening 30' formed in the proximal end 20' of the tube-shaped body 18' of the first conduit 12'. The end body portion 100' may form a passage 102' in order to permit access to the passage 28' extending through the tube-shaped body 18' of the first conduit 12'. In some instances, the passage 102' may define the proximal end adapter 94' to include a passage diameter, $D_{92}'$; the passage diameter, $D_{92}'$, of the proximal end adapter 94' may be less than the diameter, $D_{28}'$, of the passage 28' extending through the tube-shaped body 18' of the first conduit 12'. The comparatively narrower diameter, $D_{92}'$, of the proximal end adapter 94' with respect to the diameter, $D_{28}'$, of the passage 28' extending through the tube-shaped body 18' of the first conduit 12' may assist in guiding a catheter, C, into the catheter guide 10' that includes a diameter that is substantially equal to or less than the diameter, $D_{28}'$, of the passage 28' extending through the tube-shaped body 18' of the first conduit 12'.

In a substantially similar manner as described above with respect to the one or more weakened zones 84, 86, 88 of the catheter guide 10 at FIG. 6G, the arrangement of the first part 10a' and the second part 10b' of the catheter guide 10' that are selectively connected and held together by the proximal end adapter 94' and the distal end adapter 96' permits removal of the catheter guide 10' from about the catheter, C, and the penis, P, once the distal end, $C_D$, of the catheter, C, is arranged within the urinary bladder of the patient. Functionally, upon removal of the proximal end adapter 94' and the distal end adapter 96' about the first conduit 12', the first part 10a' and the second part 10b' of the catheter guide 10' may be separated from one another at the seam 90a', 90b'. Although the proximal end adapter 94' and the distal end adapter 96' are described above for functionally retaining the first part 10a' and the second part 10b' of the catheter guide 10' adjacent one another, each of the first part 10a' and the second part 10b' of the catheter guide 10' may include integrally-formed structure (e.g., a tongue-and-groove or friction-fit coupling) that permits the first part 10a' and the second part 10b' of the catheter guide 10' to be selectively releasably coupled to one another.

Figure 3B:
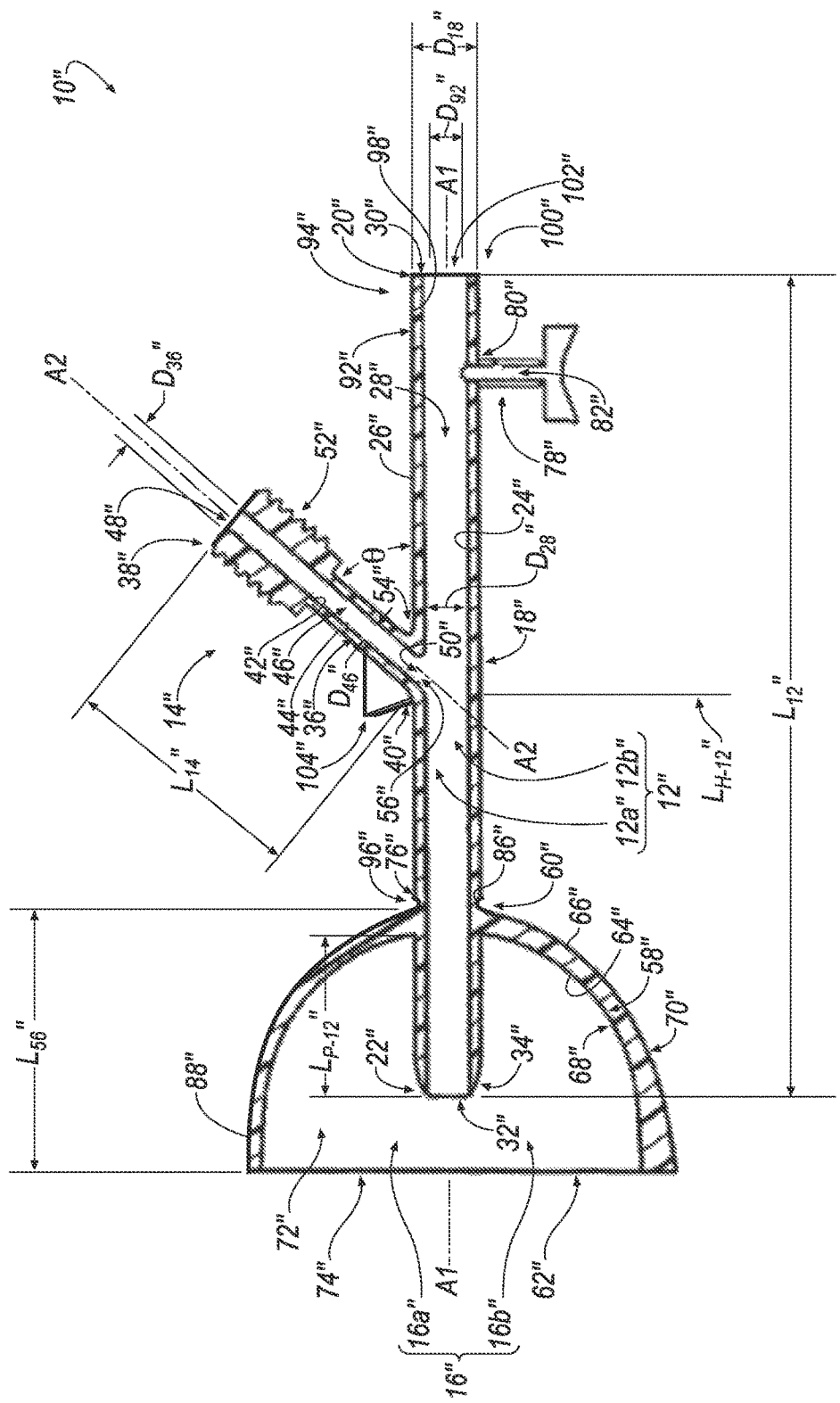
FIG. 3B is a cross-sectional view according to line 3B-3B of FIG. 3A.

Referring now to the FIGS. 3A-3C, an exemplary catheter guide is shown generally at 10". The catheter guide 10" includes a first conduit 12", a second conduit 14" and a shield member 16". The second conduit 14" is connected to the first conduit 12". The shield member 16" is connected to the first conduit 12".

The first conduit 12" includes a tube-shaped body 18" having a proximal end 20", a distal end 22", an inner surface 24" and an outer surface 26". The inner surface 24" defines a passage 28" extending through the tube-shaped body 18" from the proximal end 20" to the distal end 22". Access to the passage 28" is permitted by a proximal opening 30" formed in the proximal end 20" and a distal opening 32" formed in the distal end 22". As will be described in the following disclosure at FIGS. 6A-6G, the passage 28" may contain one or more of the catheter, C, and a fluid, F, from a syringe, S; therefore, the passage 28" may be alternatively referred to as a catheter-and-fluid-receiving passage.

The inner surface 24" may define the passage 28" to include a substantially constant passage diameter, $D_{28}"$, that extends along an entire length, $L_{12}"$, of the first conduit 12". The outer surface 26" may define the tube-shaped body 18" to include a substantially constant outer diameter, $D_{18}"$, along the entire length, $L_{12}"$, of the first conduit 12"; however, in some implementations, a portion of the outer surface 26" of the tube-shaped body 18" near, for example, the distal end 22" of the first conduit 12" may include a subtly progressively-reduced outer diameter, $D_{18}"$, thereby defining the tube-shaped body 18" to include a conical, tapered distal end portion 34"; the tapered distal end portion 34" may assist in axially aligning the distal end 22" of the first conduit 12" into the meatus, $P_O$, of the penis, P.

The second conduit 14" includes a tube-shaped body 36" having a proximal end 38", a distal end 40", an inner surface 42" and an outer surface 44". The inner surface 42" defines a passage 46" extending through the tube-shaped body 36" from the proximal end 38" to the distal end 40". Access to the passage 46" is permitted by a proximal opening 48" formed in the proximal end 38" and a distal opening 50" formed in the distal end 40". As will be described in the following disclosure at FIGS. 6A-6G, the passage 46" may permit passage of a fluid, F, from a syringe, S; therefore, the passage 46" may be alternatively referred to as a fluid-propagating passage.

The inner surface 42" may define the passage 46" to include a substantially constant passage diameter, $D_{46}"$, along an entire length, $L_{14}"$, of the second conduit 14". The outer surface 44" may define the tube-shaped body 36" to include a substantially constant outer diameter, $D_{36}"$, along the entire length, $L_{14}"$, of the second conduit 14"; however, in some implementations, a portion of the outer surface 44" of the tube-shaped body 36" near the proximal end 38" of the second conduit 14" may include an increased outer diameter, $D_{36}"$, having a threaded surface portion 52". As will be discussed in the following disclosure at FIGS. 6A-6B, the threaded surface portion 52 permits attachment of a fluid container (e.g., a syringe, F) to the second conduit 14 of the catheter guide 10. Although the portion of the outer surface 44 of the tube-shaped body 36 near the proximal end 38 of the second conduit 14 includes a threaded surface portion 52 for facilitating connection of a fluid container to the second conduit 14 of the catheter guide 10, the structure defining the tube-shaped body 36 near the proximal end 38 of the second conduit 14 may include other structure, such as, for example, a cone-shaped male-female coupling, a Luer lock or the like for facilitating attachment of fluid container (e.g., a syringe, F) to the second conduit 14 of the catheter guide 10.

The tube-shaped body 36" of the second conduit 14" is integrally-formed with and extends from the outer surface 26" of the tube-shaped body 18" of the first conduit 12". In some examples, the tube-shaped body 36" of the second conduit 14" extends from the outer surface 26" of the tube-shaped body 18" of the first conduit 12" at a region 54" near between approximately one-quarter to three-quarter (e.g., half, $L_{H-12}"$) of the length, $L_{12}"$, of the first conduit 12". In some instances, the second conduit 14" is offset from the first conduit 12" by an offset angle, θ (which may be between approximately 45° and 90°), which is referenced from a first axis, A1-A1, that extends through an axial center of the passage 28' of the first conduit 12', and, a second axis, A2-A2, that extends through an axial center of the passage 46' of the second conduit 14'.

The passage 28" extending through the first conduit 12" is fluidly-connected to the passage 46" extending through the second conduit 14". In some instances, the passage 28" is fluidly-connected to the passage 46" by way of a radial passage 56" formed in the first conduit 12" near the region 54" that is located near the middle of the length, $L_{12}"$, of the first conduit 12". In some examples, the radial passage 56" formed in the first conduit 12" may also be the distal opening 50" formed in the distal end 40" of the tube-shaped body 36" of the second conduit 14".

The shield member 16" includes a bowl-shaped body 58" having a proximal end 60", a distal end 62", an inner surface 64" and an outer surface 66". The first axis, A1-A1, extending through the axial center of the passage 28" of the first conduit 12" also extends through an axial center of the bowl-shaped body 58". The inner surface 64" of the shield member 16" defines a concave side 68" of the shield member 16" whereas the outer surface 66" of the shield member 16" defines a convex side 70" of the shield member 16". The concave side 68" defines the shield member 16" to include a glands penis-receiving cavity 72". Access to the glands penis-receiving cavity 72" is permitted by a proximal opening 74" formed in the distal end 62" of the shield member 16" and the distal opening 32" formed in the distal end 22" of the tube-shaped body 18" of the first conduit 12".

The bowl-shaped body 58" of the shield member 16" is integrally-formed with and extends from the outer surface 26" of the tube-shaped body 18" of the first conduit 12". In some examples, the bowl-shaped body 58" of the shield member 16" extends from the outer surface 26" of the tube-shaped body 18" of the first conduit 12" at a region 76" near between approximately one quarter to three-quarter (e.g., half, $L_{H-12}"$) of the length, $L_{12}"$, of the first conduit 12" and the distal end 22" of the tube-shaped body 18" of the first conduit 12". In some instances, the bowl-shaped body 58" circumscribes a portion, $L_{P-12}"$, of the length, $L_{12}"$, of the tube-shaped body 18". In some examples, the distal end 22" of the tube-shaped body 18" is arranged within the glands penis-receiving cavity 72" and does not extend beyond the distal end 62" of the bowl-shaped body 58" of the shield member 16".

Although some implementations of the shield member 16" may include bowl-shaped body 58" having an inner surface 64" and an outer surface 66" that defines, respectively, a concave side 68" and a convex side 70", the shield member 16" is not limited to a particular geometry. For example, the shield member 16" may include an inner surface and an outer surface that may extend from and be arranged substantially perpendicularly with respect to the outer surface 26" of the tube-shaped body 18" of the first conduit 12". Accordingly, in such an exemplary implementation, the inner surface may not glands penis-receiving cavity 72" but, rather, define a stop surface for limiting insertion of the length, $L_{12}"$, of the tube-shaped body 18" of the first conduit 12" to be approximately equal to the portion, $L_{P-12}$", of the length, $L_{12}$", of the tube-shaped body 18" of the first conduit 12".

In some implementations, the catheter guide 10" includes a third conduit 78" that is integrally-formed with and extends from the outer surface 26" of the tube-shaped body 18" of the first conduit 12". In some examples, the third conduit 78" extends from the outer surface 26" of the tube-shaped body 18" of the first conduit 12" at a region 80" near between approximately one-quarter to three-quarter (e.g., half, $L_{H-12}$") of the length, $L_{12}$", of the first conduit 12" and the proximal end 20" of the tube-shaped body 18" of the first conduit 12".

The third conduit 78" may be referred to as a fenestration port, which defines a pressure release passageway 82" that is in fluid communication with the passage 28" extending through the tube-shaped body 36" of the first conduit 12". Functionally, the fenestration port 78" permits a desired decompression pressure of the passage 28" extending through the tube-shaped body 36" of the first conduit 12". In some instances, a selectively-designed diameter of the pressure release passageway 82" of the fenestration port 78" permits omission of a valve element in the design of the fenestration port 78". Although the fenestration port 78" is shown extending from and arranged in fluid communication with the first conduit 12", the fenestration port 78" may be alternatively arranged in a manner extending from and being in fluid communication with the passage 46" of the second conduit 14".

The catheter guide 10" also includes one or more weakened zones 84a", 84b", 84c", 86", 88". If the one or more weakened zones 84a", 84b", 84c", 86", 88" is/are provided on the inner surface 24", 42", 64" of the first and second conduits 12", 14" and/or the shield member 16", the one or more weakened zones 84a", 84b", 84c", 86", 88" may also assist in the function of the fenestration port 78" described above.

Referring to FIG. 3A, in some implementations, the weakened zone 84a" may be arranged along the length, $L_{12}$", of the tube-shaped body 18" of the first conduit 12". The weakened zone 84a" may be a recess, groove, slot or valley that is formed in one or both of the inner surface 24" and the outer surface 26" of the tube-shaped body 18" of the first conduit 12".

Referring to FIGS. 3A-3B, in some implementations, the weakened zone 86" may be circumferentially arranged about the intersection of the tube-shaped body 18" of the first conduit 12" and the bowl-shaped body 56" of the shield member 16" near the region 76". The weakened zone 86" may be a recess, groove, slot or valley that is formed in one or more of the inner surfaces 24", 64" and the outer surfaces 26", 66" of the tube-shaped body 18" of the first conduit 12" and the bowl-shaped body 58" of the shield member 16".

Referring to FIGS. 3A-3B, in some implementations, the weakened zone 88" may be arranged along a length, $L_{56}$", of the bowl-shaped body 56" of the shield member 16". The weakened zone 88" may be a recess, groove, slot or valley that is formed in one or both of the inner surface 64" and the outer surface 66" of the bowl-shaped body 56" of the shield member 16".

The catheter guide 10" may also include a fin or grasping member 104" that extends radially outwardly from and is integrally connected to the outer surface 26" of the tube-shaped body 18" of the first conduit 12". Referring to FIG. 3C, the fin 104" may be angularly offset from the second conduit 14" by an angle, Δ1 (which may be equal to approximately 60°). With continued reference to FIG. 3C, the fin 104" may be angularly offset from the third conduit 78" by an angle, Δ2 (which may be equal to approximately 120°). With yet continued reference to FIG. 3C, the second conduit 14" may be angularly offset from the third conduit 78" by an angle, Δ3 (which may be equal to approximately 180°).

Unlike an exemplary embodiment of a catheter guide described above at FIGS. 1A-1B, in some instances, the catheter guide 10" may include more than one weakened zone arranged along the length, $L_{12}$", of the tube-shaped body 18" of the first conduit 12". For example, as seen in FIG. 3C, a first weakened zone 84a" is arranged along the length, $L_{12}$", of the tube-shaped body 18" of the first conduit 12" and is located on the outer surface 26" of the tube-shaped body 18" of the first conduit 12" between the second conduit 14" and the third conduit 78". In another example, as seen in FIG. 3C, a second weakened zone 84b" is arranged along the length, $L_{12}$", of the tube-shaped body 18" of the first conduit 12" and is located on the outer surface 26" of the tube-shaped body 18" of the first conduit 12" between the second conduit 14" and the fin 104". In yet another example, as seen in FIG. 3C, a third weakened zone 84c" is arranged along the length, $L_{12}$", of the tube-shaped body 18" of the first conduit 12" and is located on the outer surface 26" of the tube-shaped body 18" of the first conduit 12" between the fin 104" and the third conduit 78".

By arranging more than one weakened zone along the length, $L_{12}$", of the tube-shaped body 18" of the first conduit 12", a user may selectively-grasp adjacent radially-projecting structure(s) in order to selectively frangibly-break the first conduit 12" longitudinally along the length, $L_{12}$", of the tube-shaped body 18" of the first conduit 12". For example, as seen in FIG. 3C, a user may grasp the second conduit 14" and the third conduit 78" in order to frangibly-break the first conduit 12" longitudinally along the length, $L_{12}$", of the tube-shaped body 18" of the first conduit 12" at the first weakened zone 84a". In another example, as seen in FIG. 3C, a user may grasp the second conduit 14" and the fin 104" in order to frangibly-break the first conduit 12" longitudinally along the length, $L_{12}$", of the tube-shaped body 18" of the first conduit 12" at the second weakened zone 84b". In yet another example, as seen in FIG. 3C, a user may grasp the fin 104" and the third conduit 78" in order to frangibly-break the first conduit 12" longitudinally along the length, $L_{12}$", of the tube-shaped body 18" of the first conduit 12" at the third weakened zone 84c".

In a substantially similar manner as described with respect to the catheter guide 10 described at FIGS. 1A-1B as represented at FIG. 6G, the one or more weakened zones 84a", 84b", 84c", 86", 88" permit removal of the catheter guide 10" from about the catheter, C, and the penis, P, once the distal end, $C_D$, of the catheter, C, is arranged within the urinary bladder of the patient. Functionally, the one or more weakened zones 84a", 84b", 84c", 86", 88" may permit one or more of the first conduit 12" and the shield member 16" to be frangible such that, for example: (1) the first conduit 12" may be split apart along the length, $L_{12}$", of the first conduit 12" as a result of the inclusion of the one or more of the weakened zones 84a", 84b", 84c", (2) the first conduit 12" may be separated from the shield member 16" as a result of the inclusion of the weakened zone 86", and (3) the shield member 16" may be split apart along the length, $L_{56}$", of the shield member 16" as a result of the inclusion of the weakened zone 88".

Referring now to the FIG. 4, an exemplary catheter guide is shown generally at 10'''. The catheter guide 10''' includes a first conduit 12''', a second conduit 14''' and a shield member 16'''. The second conduit 14''' is connected to the first conduit 12'''. The shield member 16''' is connected to the first conduit 12'''.

The first conduit 12''' includes a tube-shaped body 18''' having a proximal end 20''', a distal end 22''', an inner surface (not shown but substantially similar to, for example, the inner surface 24 described above) and an outer surface 26'''. The inner surface defines a passage (not shown but substantially similar to, for example, the passage 28 described above) extending through the tube-shaped body 18''' from the proximal end 20''' to the distal end 22'''. Access to the passage is permitted by a proximal opening 30''' formed in the proximal end 20''' and a distal opening 32''' formed in the distal end 22'''. As will be described in the following disclosure at FIGS. 6A-6G, the passage may contain one or more of the catheter, C, and a fluid, F, from a syringe, S; therefore, the passage may be alternatively referred to as a catheter-and-fluid-receiving passage.

The inner surface may define the passage to include a substantially constant passage diameter (not shown but substantially similar to, for example, the diameter, $D_{28}$, described above) that extends along an entire length, $L_{12}'''$, of the first conduit 12'''. The outer surface 26''' may define the tube-shaped body 18''' to include a substantially constant outer diameter, $D_{18}'''$, along the entire length, $L_{12}'''$, of the first conduit 12'''; however, in some implementations, a portion of the outer surface 26''' of the tube-shaped body 18''' near, for example, the distal end 22''' of the first conduit 12''' may include a subtly progressively-reduced outer diameter, $D_{18}'''$, thereby defining the tube-shaped body 18''' to include a conical, tapered distal end portion 34'''; the tapered distal end portion 34''' may assist in axially aligning the distal end 22''' of the first conduit 12''' into the meatus, $P_O$, of the penis, P.

The second conduit 14''' includes a tube-shaped body 36''' having a proximal end 38''', a distal end 40''', an inner surface (not shown but substantially similar to, for example, the inner surface 42 described above) and an outer surface 44'''. The inner surface defines a passage (not shown but substantially similar to, for example, the passage 46 described above) extending through the tube-shaped body 36''' from the proximal end 38''' to the distal end 40'''. Access to the passage is permitted by a proximal opening (not shown but substantially similar to, for example, the proximal opening 48 described above) formed in the proximal end 38''' and a distal opening (not shown but substantially similar to, for example, the distal opening 50 described above) formed in the distal end 40'''. As will be described in the following disclosure at FIGS. 6A-6G, the passage may permit passage of a fluid, F, from a syringe, S; therefore, the passage may be alternatively referred to as a fluid-propagating passage.

The inner surface may define the passage to include a substantially constant passage diameter (not shown but substantially similar to, for example, the passage diameter, $D_{46}$, described above) along an entire length, $L_{14}'''$, of the second conduit 14'''. The outer surface 44''' may define the tube-shaped body 36''' to include a substantially constant outer diameter, $D_{36}'''$, along the entire length, $L_{14}'''$, of the second conduit 14'''; however, in some implementations, a portion of the outer surface 44''' of the tube-shaped body 36''' near the proximal end 38''' of the second conduit 14''' may include an increased outer diameter, $D_{36}'''$, having a threaded surface portion (not shown but substantially similar to, for example, the threaded surface portion 52 described above). As will be discussed in the following disclosure at FIGS. 6A-6B, the threaded surface portion permits attachment of a fluid container (e.g., a syringe, F) to the second conduit 14 of the catheter guide 10. Although the portion of the outer surface 44 of the tube-shaped body 36 near the proximal end 38 of the second conduit 14 includes a threaded surface portion for facilitating connection of a fluid container to the second conduit 14 of the catheter guide 10, the structure defining the tube-shaped body 36 near the proximal end 38 of the second conduit 14 may include other structure, such as, for example, a cone-shaped male-female coupling, a Luer lock or the like for facilitating attachment of fluid container (e.g., a syringe, F) to the second conduit 14 of the catheter guide 10.

The tube-shaped body 36''' of the second conduit 14''' is integrally-formed with and extends from the outer surface 26''' of the tube-shaped body 18''' of the first conduit 12'''. In some examples, the tube-shaped body 36''' of the second conduit 14''' extends from the outer surface 26''' of the tube-shaped body 18''' of the first conduit 12''' at a region 54''' near between approximately one-quarter to three-quarter (e.g., half, $L_{H-12}'''$) of the length, $L_{12}'''$, of the first conduit 12'''. In some instances, the second conduit 14''' is offset from the first conduit 12''' by an offset angle, θ (which may be between approximately 45° and 90°), which is referenced from a first axis, A1-A1, that extends through an axial center of the passage of the first conduit 12''', and, a second axis, A2-A2, that extends through an axial center of the passage of the second conduit 14'''.

The passage extending through the first conduit 12''' is fluidly-connected to the passage extending through the second conduit 14'''. In some instances, the passage extending through the first conduit 12''' is fluidly-connected to the passage extending through the second conduit 14''' by way of a radial passage (not shown but substantially similar to, for example, the radial passage 56 described above) formed in the first conduit 12''' near the region 54''' that is located near the middle of the length, $L_{12}'''$, of the first conduit 12'''. In some examples, the radial passage formed in the first conduit 12''' may also be the distal opening formed in the distal end 40''' of the tube-shaped body 36''' of the second conduit 14'''.

The shield member 16''' includes a bowl-shaped body 58''' having a proximal end 60''', a distal end 62''', an inner surface 64''' and an outer surface 66'''. The first axis, A1-A1, extending through the axial center of the passage of the first conduit 12''' also extends through an axial center of the bowl-shaped body 58'''. The inner surface 64''' of the shield member 16''' defines a substantially concave side 68''' of the shield member 16''' whereas the outer surface 66''' of the shield member 16''' defines a convex side 70''' of the shield member 16'''. The concave side 68''' defines the shield member 16''' to include a glands penis-receiving cavity 72'''. Access to the glands penis-receiving cavity 72''' is permitted by a proximal opening 74''' formed in the distal end 62''' of the shield member 16''' and the distal opening 32''' formed in the distal end 22''' of the tube-shaped body 18''' of the first conduit 12'''.

Unlike exemplary embodiments of catheter guides discussed above at FIGS. 1A-3C, the bowl-shaped body 58''' of the shield member 16''' may be not integrally-formed with the outer surface 26''' of the tube-shaped body 18''' of the first conduit 12'''; rather, the bowl-shaped body 58''' is a non-rigid, flexible sheet that is separately-formed with respect to the first conduit 12''' and may be selectively-secured thereto with the assistance of, for example, an adapter 96'''. In some implementations, the shield member 16''' may be integrally-formed with the outer surface 26''' of the tube-shaped body 18''' of the first conduit 12''' such that the adapter 96''' is not included in the design of the catheter guide 10'''; if the shield member 16''' is integrally-formed with the first conduit 12''', the non-rigid, flexible sheet may be defined to have an overall reduced thickness that is frangible/tearable at any location without having to form one or weakened zones that is/are substantially similar to the weakened zone 88 described above. In other implementations, the shield member 16''' may be formed of a single continuous sheet having overlapping edges that may be held together with, for example, an adhesive that will permit a user to selectively peel-apart the overlapping edges in order to remove the shield member 16''' from the first conduit 12'''; in other implementations, the overlapping edges of the single continuous sheet may be manually held together by hand and therefore an exemplary use of an adhesive may be obviated.

The adapter 96''' may be, for example, an elastic band. Further, the bowl-shaped body 58''' may include a proximal opening that permits insertion of the distal end 32''' of the tube-shaped body 18''' of the first conduit 12''' into the glands penis-receiving cavity 72''' of the bowl-shaped body 58'''; once the distal end 32''' of the tube-shaped body 18''' of the first conduit 12''' is inserted through the proximal opening of the bowl-shaped body 58''', the adapter 96''' may be arranged about the outer surface 66''' of the shield member 16''' for selectively-securing the shield member 16''' to the outer surface 26''' of the tube-shaped body 18''' of the first conduit 12''' such that the inner surface 64''' of the bowl-shaped body 58''' of the shield member 16''' is selectively-pressed adjacent the outer surface 26''' of the tube-shaped body 18''' of the first conduit 12'''. In some examples, the bowl-shaped body 58''' of the shield member 16''' extends from the outer surface 26''' of the tube-shaped body 18''' of the first conduit 12''' at a region 76''' near between approximately one-quarter to three-quarter (e.g., half, $L_{H\text{-}12}$''') of the length, $L_{12}$''', of the first conduit 12''' and the distal end 22''' of the tube-shaped body 18''' of the first conduit 12'''. In some instances, the bowl-shaped body 58''' circumscribes a portion, $L_{P\text{-}12}$''', of the length, $L_{12}$''', of the tube-shaped body 18'''. In some examples, the distal end 22''' of the tube-shaped body 18''' is arranged within the glands penis-receiving cavity 72''' and does not extend beyond the distal end 62''' of the bowl-shaped body 58''' of the shield member 16'''.

In some implementations, the proximal opening of the bowl-shaped body 58''' may be formed with a rigid member having an outer diameter that is slightly less than the outer diameter, $D_{18}$''', of the tube-shaped body 18 of the guide conduit 12. In such an exemplary implementation, the rigid member of the bowl-shaped body 58''' may be friction-fit into the passage 28 of the tube-shaped body 18 of the guide conduit 12 in order to omit the adapter 96''' from the design of the catheter guide 10'''.

Although some implementations of the shield member 16''' may include bowl-shaped body 58''' having an inner surface 64''' and an outer surface 66''' that defines, respectively, a concave side 68''' and a convex side 70''', the shield member 16''' is not limited to a particular geometry. For example, the shield member 16''' may include an inner surface and an outer surface that may extend from and be arranged substantially perpendicularly with respect to the outer surface 26''' of the tube-shaped body 18''' of the first conduit 12'''. Accordingly, in such an exemplary implementation, the inner surface may not glands penis-receiving cavity 72''' but, rather, define a stop surface for limiting insertion of the length, $L_{12}$''', of the tube-shaped body 18''' of the first conduit 12''' to be approximately equal to the portion, $L_{P\text{-}12}$''', of the length, $L_{12}$''', of the tube-shaped body 18''' of the first conduit 12'''.

In some implementations, the catheter guide 10''' includes a third conduit 78''' that is integrally-formed with and extends from the outer surface 26''' of the tube-shaped body 18''' of the first conduit 12'''. In some examples, the third conduit 78''' extends from the outer surface 26''' of the tube-shaped body 18''' of the first conduit 12''' at a region 80''' near between approximately one-quarter to three-quarter (e.g., half, $L_{H\text{-}12}$''') of the length, $L_{12}$''', of the first conduit 12''' and the proximal end 20''' of the tube-shaped body 18''' of the first conduit 12'''.

The third conduit 78''' may be referred to as a fenestration port, which defines a pressure release passageway (not shown but substantially similar to, for example, the pressure release passageway 82 described above) that is in fluid communication with the passage extending through the tube-shaped body 36''' of the first conduit 12'''. Functionally, the fenestration port 78''' permits a desired decompression pressure of the passage extending through the tube-shaped body 36''' of the first conduit 12'''. In some instances, a selectively-designed diameter of the pressure release passageway of the fenestration port 78''' permits omission of a valve element in the design of the fenestration port 78'''. Although the fenestration port 78''' is shown extending from and arranged in fluid communication with the first conduit 12''', the fenestration port 78''' may be alternatively arranged in a manner extending from and being in fluid communication with the passage of the second conduit 14'''.

The catheter guide 10''' also includes one or more weakened zones 84'''. If the one or more weakened zones 84''' is/are provided on the inner surface of the first and second conduits 12''', 14''', the one or more weakened zones 84''' may also assist in the function of the fenestration port 78''' described above.

In some implementations, the weakened zone 84''' may be arranged along the length, $L_{12}$''', of the tube-shaped body 18''' of the first conduit 12'''. The weakened zone 84''' may be a recess, groove, slot or valley that is formed in one or both of the inner surface and the outer surface of the tube-shaped body 18''' of the first conduit 12'''.

In a substantially similar manner as described above with respect to the one or more weakened zones 84, 86, 88 of the catheter guide 10 at FIG. 6G, the one or more weakened zones 84''' permit removal of the catheter guide 10''' from about the catheter, C, and the penis, P, once the distal end, $C_D$, of the catheter, C, is arranged within the urinary bladder of the patient. Functionally, the one or more weakened zones 84''' may permit the first conduit 12''' to be frangible such that, for example, the first conduit 12''' may be split apart along the length, $L_{12}$''', of the first conduit 12''' as a result of the inclusion of the weakened zone 84'''. Prior to splitting apart the first conduit 12''' along its length, $L_{12}$''', the shield member 16''' may be selectively-detached from the first conduit 12''' upon removing the adapter 96'''.

Referring now to the FIG. 5, an exemplary catheter guide is shown generally at 10''''. The catheter guide 10'''' includes a first conduit 12'''', a second conduit 14'''' and a shield member 16''''. The second conduit 14'''' is connected to both of the first conduit 12'''' and the shield member 16''''. The shield member 16'''' is connected to the first conduit 12''''.

The first conduit 12'''' includes a tube-shaped body 18'''' having a proximal end (not shown but substantially similar to, for example, the proximal end 20 described above), a distal end 22'''', an inner surface 24'''' and an outer surface 26''''. The inner surface 24'''' defines a passage 28'''' extending through the tube-shaped body 18"" from the proximal end to the distal end 22"". Access to the passage 28"" is permitted by a proximal opening (not shown but substantially similar to, for example, the proximal opening 30 described above) formed in the proximal end and a distal opening 32"" formed in the distal end 22"". As will be described in the following disclosure at FIGS. 6A-6G, the passage 28"" may contain one or more of the catheter, C, and a fluid, F, from a syringe, S; therefore, the passage 28"" may be alternatively referred to as a catheter-and-fluid-receiving passage.

The inner surface 24"" may define the passage 28"" to include a substantially constant passage diameter, $D_{28}""$, that extends along an entire length, $L_{12}""$, of the first conduit 12"". The outer surface 26"" may define the tube-shaped body 18"" to include a substantially constant outer diameter, $D_{18}""$, along the entire length (not shown but substantially similar to, for example, the length, $L_{12}$, described above) of the first conduit 12""; however, in some implementations, a portion of the outer surface 26"" of the tube-shaped body 18"" near, for example, the distal end 22"" of the first conduit 12"" may include a subtly progressively-reduced outer diameter thereby defining the tube-shaped body 18"" to include a conical, tapered distal end portion 34""; the tapered distal end portion 34"" may assist in axially aligning the distal end 22"" of the first conduit 12"" into the meatus, $P_O$, of the penis, P.

The second conduit 14"" includes a tube-shaped body 36"" having a proximal end 38"", a distal end 40"", an inner surface 42"" and an outer surface 44"". The inner surface 42"" defines a passage 46"" extending through the tube-shaped body 36"" from the proximal end 38"" to the distal end 40"". Access to the passage 46"" is permitted by a proximal opening 48"" formed in the proximal end 38"" and a distal opening 50"" formed in the distal end 40"". As will be described in the following disclosure at FIGS. 6A-6G, the passage 46"" may permit passage of a fluid, F, from a syringe, S; therefore, the passage 46"" may be alternatively referred to as a fluid-propagating passage.

The inner surface 42"" may define the passage 46"" to include a substantially constant passage diameter (not shown but substantially similar to, for example, the passage diameter, $D_{46}$, described above) along an entire length (not shown but substantially similar to, for example, the length, $L_{14}$, described above) of the second conduit 14"". The outer surface 44"" may define the tube-shaped body 36"" to include a substantially constant outer diameter (not shown but substantially similar to, for example, the outer diameter, $D_{36}$, described above) along the entire length of the second conduit 14""; however, in some implementations, a portion of the outer surface 44"" of the tube-shaped body 36"" near the proximal end 38"" of the second conduit 14"" may include an increased outer diameter having a threaded surface portion 52"". As will be discussed in the following disclosure at FIGS. 6A-6B, the threaded surface portion 52 permits attachment of a fluid container (e.g., a syringe, F) to the second conduit 14 of the catheter guide 10. Although the portion of the outer surface 44 of the tube-shaped body 36 near the proximal end 38 of the second conduit 14 includes a threaded surface portion 52 for facilitating connection of a fluid container to the second conduit 14 of the catheter guide 10, the structure defining the tube-shaped body 36 near the proximal end 38 of the second conduit 14 may include other structure, such as, for example, a cone-shaped male-female coupling, a Luer lock or the like for facilitating attachment of fluid container (e.g., a syringe, F) to the second conduit 14 of the catheter guide 10.

The tube-shaped body 36"" of the second conduit 14"" is integrally-formed with and extends from the outer surface 26"" of the tube-shaped body 18"" of the first conduit 12"". In some examples, the tube-shaped body 36"" of the second conduit 14 extends from the outer surface 26"" of the tube-shaped body 18"" of the first conduit 12"" at a region 54"" within a glands penis-receiving cavity 72"" of the shield member 16""; as a result, the second conduit 14"" extends through a passage formed in a bowl-shaped body 58"" of the shield member 16"". In some instances, the second conduit 14"" is offset from the first conduit 12"" by an offset angle (not shown but substantially similar to, for example, the offset angle, θ, described above, which may be between approximately 45° and 90°), which is referenced from a first axis, A1-A1, that extends through an axial center of the passage 28"" of the first conduit 12"", and, a second axis, A2-A2, that extends through an axial center of the passage 46"" of the second conduit 14"".

The passage 28"" extending through the first conduit 12"" is fluidly-connected to the passage 46"" extending through the second conduit 14"". In some instances, the passage 28"" is fluidly-connected to the passage 46"" by way of a radial passage 56"" formed in the first conduit 12"" near the region 54"" within the glands penis-receiving cavity 72"" of the shield member 16"". In some examples, the radial passage 56"" formed in the first conduit 12"" may also be the distal opening 50"" formed in the distal end 40"" of the tube-shaped body 36"" of the second conduit 14"".

The shield member 16"" includes a bowl-shaped body 58"" having a proximal end 60"", a distal end 62"", an inner surface 64"" and an outer surface 66"". The first axis, A1-A1, extending through the axial center of the passage 28"" of the first conduit 12"" also extends through an axial center of the bowl-shaped body 58"". The inner surface 64"" of the shield member 16"" defines a concave side 68"" of the shield member 16"" whereas the outer surface 66"" of the shield member 16"" defines a convex side 70"" of the shield member 16"". The concave side 68"" defines the shield member 16"" to include a glands penis-receiving cavity 72"". Access to the glands penis-receiving cavity 72"" is permitted by a proximal opening 74"" formed in the distal end 62"" of the shield member 16"" and the distal opening 32"" formed in the distal end 22"" of the tube-shaped body 18"" of the first conduit 12"".

The bowl-shaped body 58"" of the shield member 16"" is integrally-formed with and extends from the outer surface 26"" of the tube-shaped body 18"" of the first conduit 12"". In some examples, the bowl-shaped body 58"" of the shield member 16"" extends from the outer surface 26"" of the tube-shaped body 18"" of the first conduit 12"" at a region (not shown but substantially similar to, for example, the region 76 described above) near between approximately one-quarter to three-quarter (e.g., half) of the length of the first conduit 12"" and the distal end 22"" of the tube-shaped body 18"" of the first conduit 12"". In some instances, the bowl-shaped body 58"" circumscribes a portion (not shown but substantially similar to, for example, the portion, $L_{P-12}$, described above) of the length of the tube-shaped body 18"". In some examples, the distal end 22"" of the tube-shaped body 18''' is arranged outside of the glands penis-receiving cavity 72"" and extends beyond the distal end 62"" of the bowl-shaped body 58"" of the shield member 16"".

Although some implementations of the shield member 16"" may include bowl-shaped body 58"" having an inner surface 64"" and an outer surface 66"" that defines, respectively, a concave side 68"" and a convex side 70"", the shield member 16"" is not limited to a particular geometry. For example, the shield member 16'''' may include an inner surface and an outer surface that may extend from and be arranged substantially perpendicularly with respect to the outer surface 26'''' of the tube-shaped body 18'''' of the first conduit 12''''. Accordingly, in such an exemplary implementation, the inner surface may not glands penis-receiving cavity 72'''' but, rather, define a stop surface for limiting insertion of the length, $L_{12}$'''', of the tube-shaped body 18'''' of the first conduit 12'''' to be approximately equal to the portion, $L_{P-12}$'''', of the length, $L_{12}$'''', of the tube-shaped body 18'''' of the first conduit 12''''.

In some implementations, the catheter guide 10'''' includes a third conduit (not shown but substantially similar to, for example, the third conduit 78 described above) that is integrally-formed with and extends from the outer surface 26'''' of the tube-shaped body 18'''' of the first conduit 12''''. In some examples, the third conduit 78'''' extends from the outer surface 26'''' of the tube-shaped body 18'''' of the first conduit 12'''' at a region (not shown but substantially similar to, for example, the region 80 described above) near between approximately one-quarter to three-quarter (e.g., half) of the length of the first conduit 12'''' and the proximal end of the tube-shaped body 18'''' of the first conduit 12''''.

The third conduit may be referred to as a fenestration port, which defines a pressure release passageway (not shown but substantially similar to, for example, the pressure release passageway 82 described above) that is in fluid communication with the passage 28'''' extending through the tube-shaped body 36'''' of the first conduit 12''''. Functionally, the fenestration port permits a desired decompression pressure of the passage 28'''' extending through the tube-shaped body 36'''' of the first conduit 12''''. In some instances, a selectively-designed diameter of the pressure release passageway of the fenestration port permits omission of a valve element in the design of the fenestration port. Although the fenestration port is shown extending from and arranged in fluid communication with the first conduit 12'''', the fenestration port may be alternatively arranged in a manner extending from and being in fluid communication with the passage 46'''' of the second conduit 14''''.

The catheter guide 10'''' also includes one or more weakened zones 86'''' and 88''''. Although not shown, the catheter guide 10'''' may also include one or more weakened zones substantially similar to, for example, the weakened zone 84 described above. If the one or more weakened zones 86'''', 88'''' is/are provided on the inner surface 24'''', 42'''', 64'''' of the first and second conduits 12'''', 14'''' and/or the shield member 16'''', the one or more weakened zones 86'''', 88'''' may also assist in the function of the fenestration port described above.

In some implementations, the weakened zone (not shown but substantially similar to, for example, the weakened zone 84 described above) may be arranged along the length of the tube-shaped body 18'''' of the first conduit 12''''. The weakened zone may be a recess, groove, slot or valley that is formed in one or both of the inner surface 24'''' and the outer surface 26'''' of the tube-shaped body 18'''' of the first conduit 12''''.

In some implementations, the weakened zone 86'''' may be circumferentially arranged about the intersection of the tube-shaped body 18'''' of the first conduit 12'''' and the bowl-shaped body 56'''' of the shield member 16'''' near the region 76''''. The weakened zone 86'''' may be a recess, groove, slot or valley that is formed in one or more of the inner surfaces 24'''', 64'''' and the outer surfaces 26'''', 66'''' of the tube-shaped body 18'''' of the first conduit 12'''' and the bowl-shaped body 58'''' of the shield member 16''''.

In some implementations, the weakened zone 88'''' may be arranged along a length (not shown but substantially similar to, for example, the length, $L_{56}$, describe above) of the bowl-shaped body 56'''' of the shield member 16''''. The weakened zone 88'''' may be a recess, groove, slot or valley that is formed in one or both of the inner surface 64'''' and the outer surface 66'''' of the bowl-shaped body 56'''' of the shield member 16''''.

In a substantially similar manner as described above with respect to the one or more weakened zones 84, 86, 88 of the catheter guide 10 at FIG. 6G, the one or more weakened zones 86'''', 88'''' permit removal of the catheter guide 10'''' from about the catheter, C, and the penis, P, once the distal end, $C_D$, of the catheter, C, is arranged within the urinary bladder of the patient. Functionally, the one or more weakened zones 86'''', 88'''' may permit one or more of the first conduit 12'''' and the shield member 16'''' to be frangible such that, for example: (1) the first conduit 12'''' may be split apart along the length of the first conduit 12'''' as a result of the inclusion of the weakened zone (not shown but substantially similar to, for example, the weakened zone 84 described above), (2) the first conduit 12'''' may be separated from the shield member 16'''' as a result of the inclusion of the weakened zone 86'''', and (3) the shield member 16'''' may be split apart along the length of the shield member 16'''' as a result of the inclusion of the weakened zone 88''''.

Referring to FIGS. 6A-6G, a method for utilizing the catheter guide 10 is described as follows. Although the method is described in conjunction with the catheter guide 10 described above at FIGS. 1A-1B, the method is equally applicable to the catheter guides 10', 10'', 10''', 10'''' described above at FIGS. 2A-5.

Referring to FIG. 6A, a manually-operable syringe, S, may be releasably connected to the second conduit 14. In an example, a distal end, $S_D$, of the syringe may include an inner threaded surface, $S_T$, that corresponds to the threaded surface portion 52 of the outer surface 44 of the tube-shaped body 36 near the proximal end 38 of the second conduit 14 such that the syringe, S, may be releasably-coupled to the catheter guide 10 at the second conduit 14.

Figure 6B:
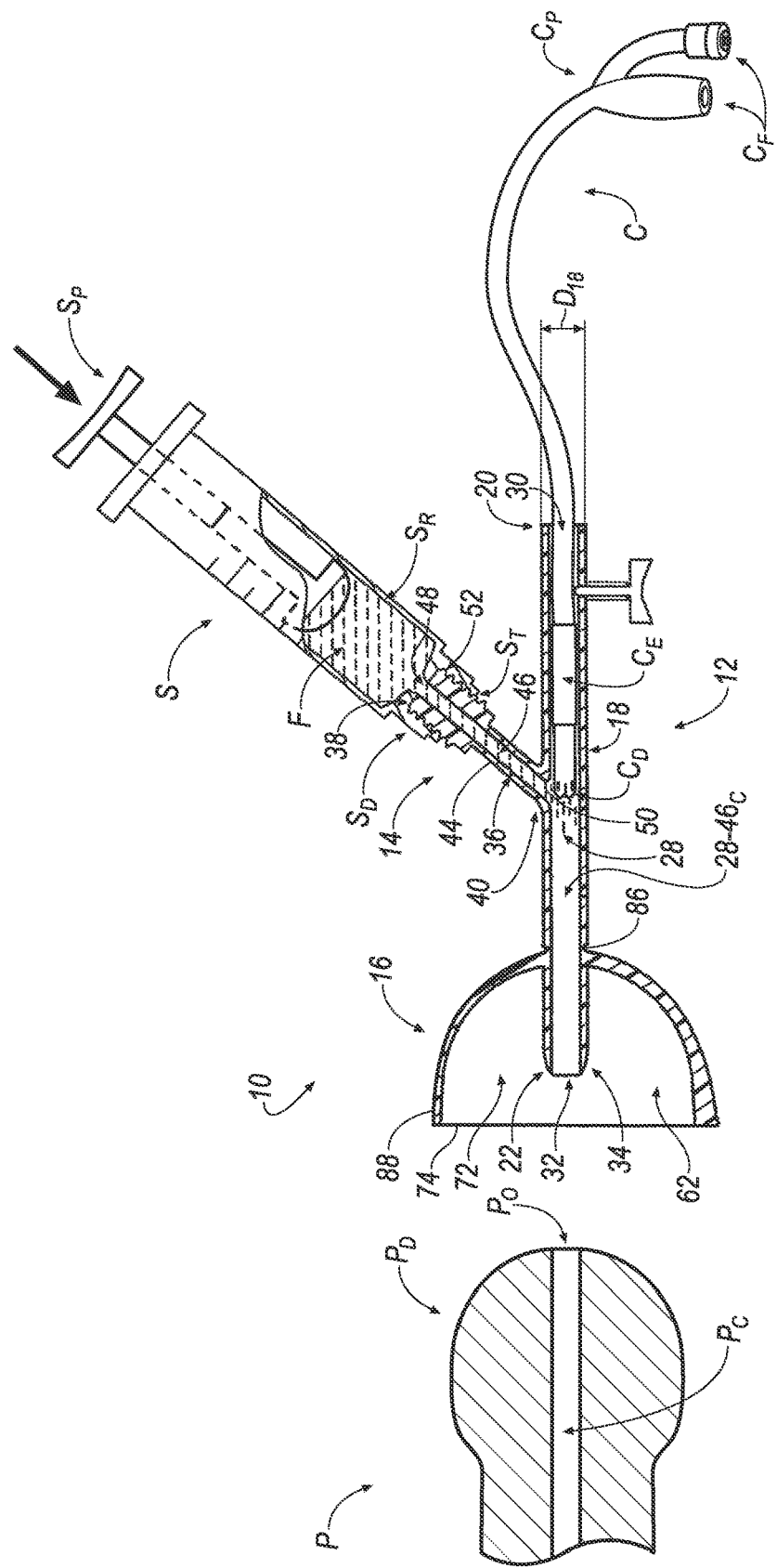

Referring to FIG. 6B, once the syringe, S, is directly interfaced with the catheter guide 10 as described above, the catheter, C, may be interfaced with the catheter guide 10. Firstly, as seen in FIG. 6A, the distal end, $C_D$, of the catheter, C, may be axially aligned with the proximal opening 30 formed in the proximal end 20 of the tube-shaped body 18 of the first conduit 12. Then, as seen in FIG. 6B, the distal end, $C_D$, of the catheter, C, may be axially inserted into the passage 28 formed by the tube-shaped body 18 of the first conduit 12. The distal end, $C_D$, of the catheter, C, is guided into the passage 28 until the distal end, $C_D$, of the catheter, C, is arranged proximate, near, but not beyond the distal opening 50 formed in the distal end 40 of the tube-shaped body 36 of the second conduit 14. A portion (e.g., the expandable member, $C_E$) of the catheter, C, that is near the distal end, $C_D$, of the catheter, C, may at least partially fluidly-seal a portion of the passage 28 to thereby define a fluid sub-chamber 28-46$_C$ of the catheter, C, defined by all of the passage 46 extending through the second conduit 14 and a portion of the passage 28 extending through the first conduit 14 between the distal opening 32 formed at the distal end 22 of the first conduit 12 and the distal opening 50 formed at the distal end 40 of the second conduit 14.

Upon the distal end, $C_D$, of the catheter, C, being advanced proximate, near, but not beyond the distal opening 50 formed in the distal end 40 of the tube-shaped body 36 of the second conduit 14, the user (e.g., a nurse) may partially depress a plunger, $S_P$, that is movably received within a fluid reservoir chamber, $S_R$, of the syringe, S. By depressing the plunger, $S_P$, a portion of a fluid, F (such as, e.g., a surgical grade or medical grade viscous lubricating fluid, a disinfectant, a local anesthetic, water, saline, or the like), contained within the fluid reservoir chamber, $S_R$, is evacuated into the fluid sub-chamber $28\text{-}46_C$. Once the fluid, F, has arrived in the fluid sub-chamber $28\text{-}46_C$, the fluid, F, may be prevented from exiting the proximal opening 30 of the catheter guide 10 and coat at least the distal end, $C_D$, of the catheter, C.

Figure 6C:
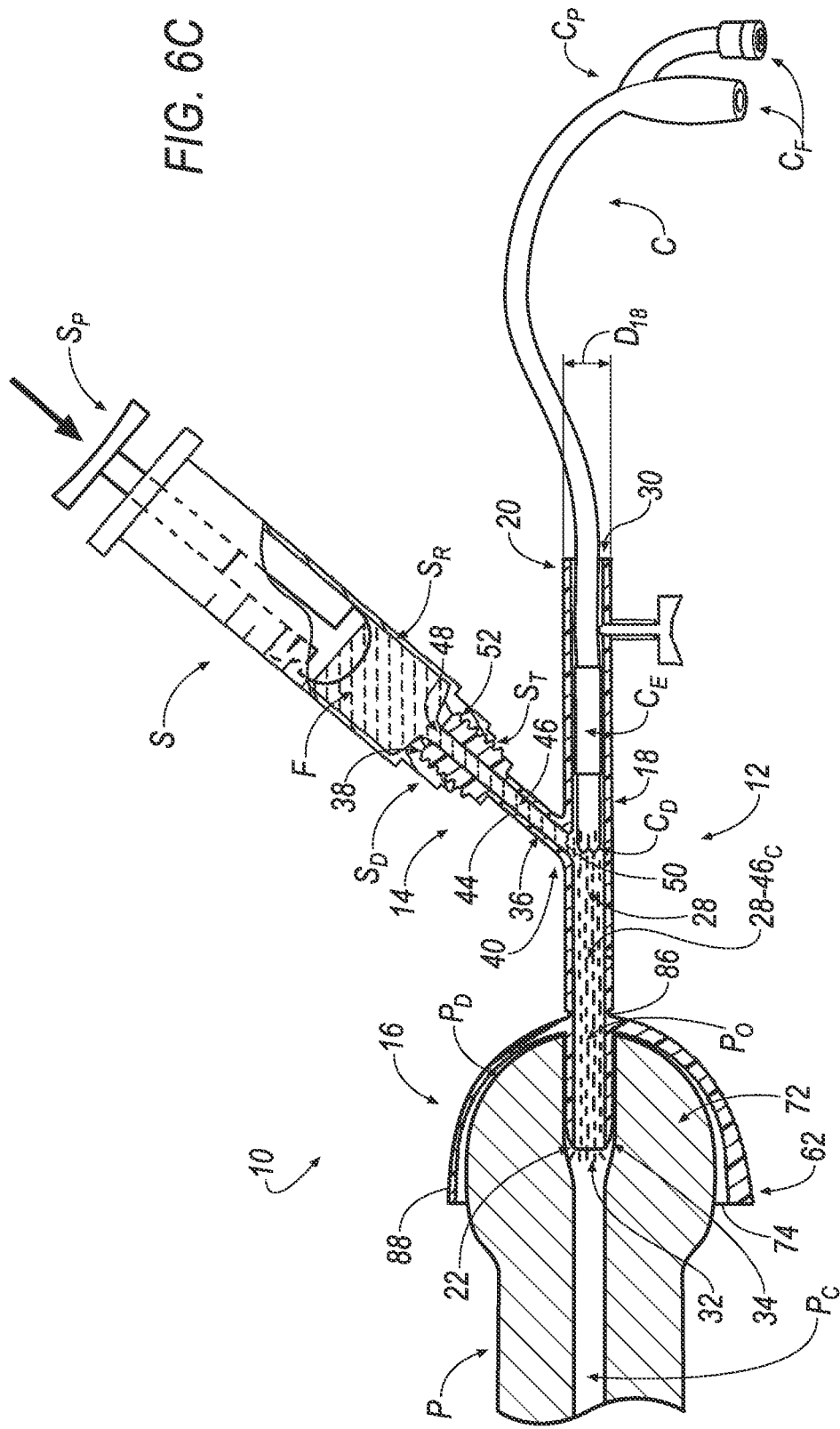

Referring to FIG. 6C, before or after evacuating a portion of the fluid, F, into the fluid sub-chamber $28\text{-}46_C$, the user (e.g., a nurse) may arrange the proximal opening 74 formed in the distal end 62 of the shield member 16 opposite the glands penis, $P_D$, of the penis, P, while axially aligning the distal end 22 of the tube-shaped body 18 of the first conduit 12 of the catheter guide 10 with the meatus, $P_O$, of the penis, P. After arranging the catheter guide 10 relative the penis, P, as described above, the catheter guide 10 may then be directly interfaced with the penis, P, such that the glands penis, $P_D$, of the penis, P, is disposed within the glands penis-receiving cavity 72 of the shield member 16. As a result of the axial alignment of the distal end 22 of the tube-shaped body 18 of the first conduit 12 of the catheter guide 10 with the meatus, $P_O$, of the penis, P, as described above, once the catheter guide 10 is directly interfaced with the penis, P, the distal end 22 of the tube-shaped body 18 of the first conduit 12 may be disposed within the urethra, $P_C$, of the penis, P, near the meatus, $P_O$, of the penis, P; as a result of the arrangement of the catheter guide 10 relative the penis, P, as described above, the opening 32 formed in the distal end 22 of the tube-shaped body 18 of the first conduit 12 is in direct fluid communication with the urethra, $P_C$, of the penis, P, to thereby permit the fluid sub-chamber $28\text{-}46_C$ to be in fluid communication with the urethra, $P_C$, of the penis, P.

Then, as seen in FIG. 6C, the user may depress the plunger, $S_P$, of the syringe, S, in order to evacuate the fluid, F, into the fluid sub-chamber $28\text{-}46_C$ such that the fluid, F, is evacuated into the passage 46 extending through the tube-shaped body 36 of the second conduit 14 by way of the proximal opening 48 formed in the proximal end 38 of the tube-shaped body 36 of the second conduit 14 for subsequent discharge out of the distal opening 50 formed in the distal end 40 of the tube-shaped body 36 of the second conduit 14 such that the fluid, F, is deposited into the passage 28 formed by the tube-shaped body 18 of the first conduit 12. Once the fluid, F, has arrived in the passage 28 formed by the tube-shaped body 18 of the first conduit 12, the fluid, F, is further advanced toward the opening 32 formed in the distal end 22 of the tube-shaped body 18 of the first conduit 12 that is in direct fluid communication with the urethra, $P_C$, of the penis, P, to thereby permit the fluid, F, to enter the urethra, $P_C$, of the penis, P, due to the fluid sub-chamber $28\text{-}46_C$ being in fluid communication with the urethra, $P_C$, of the penis, P. Because the distal end 22 of the tube-shaped body 18 of the first conduit 12 is disposed within the urethra, $P_C$, of the penis, P, the catheter guide 10 directly guides the fluid, F, into the urethra, $P_C$, of the penis, P, and therefore inhibits the fluid, F, from being disposed about an exterior surface of the penis, P, prior to insertion of the distal end, $C_D$, of the catheter, C, into the meatus, $P_O$, of the penis, P.

Figure 6D:
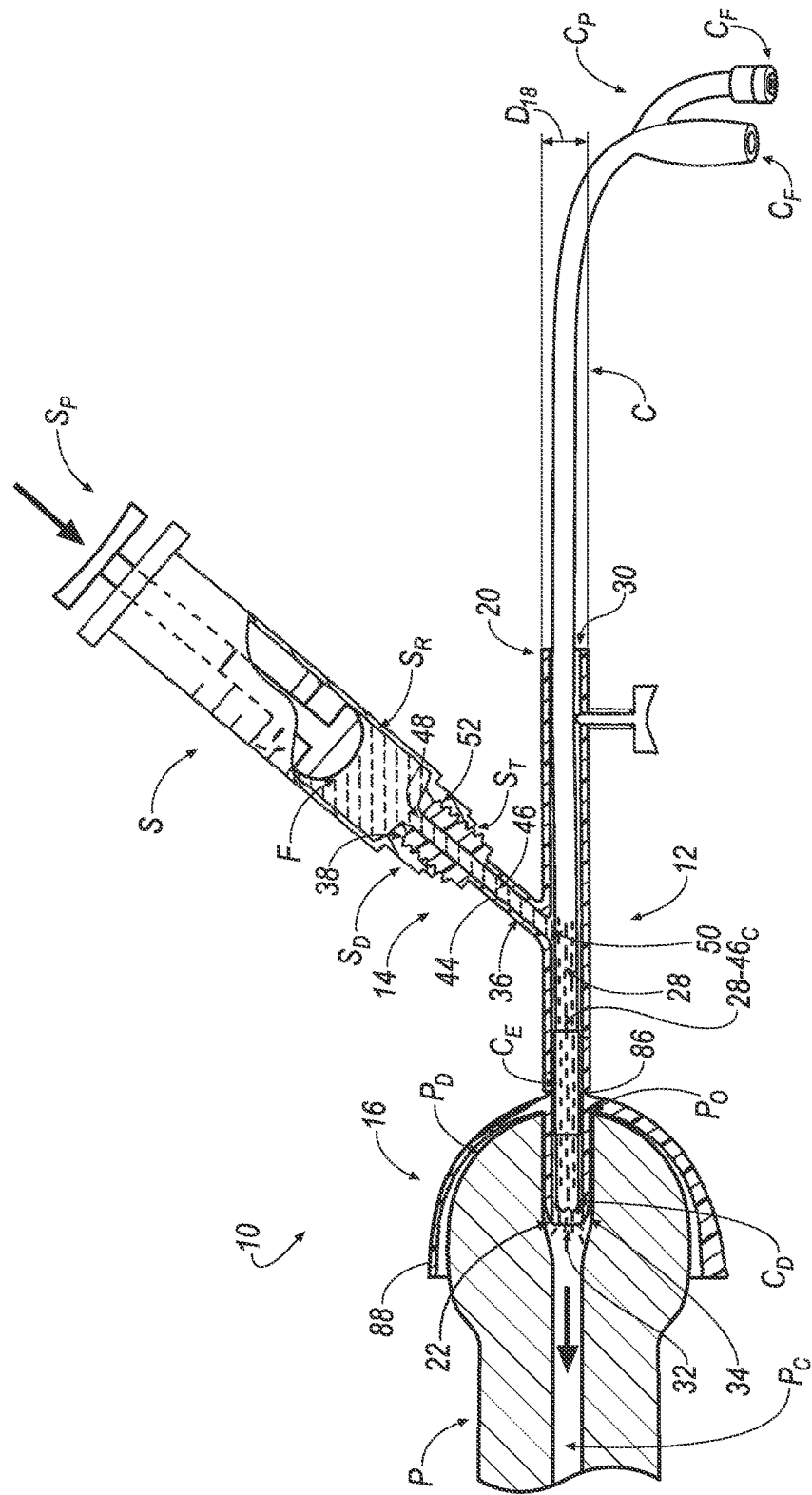
Figure 6E:
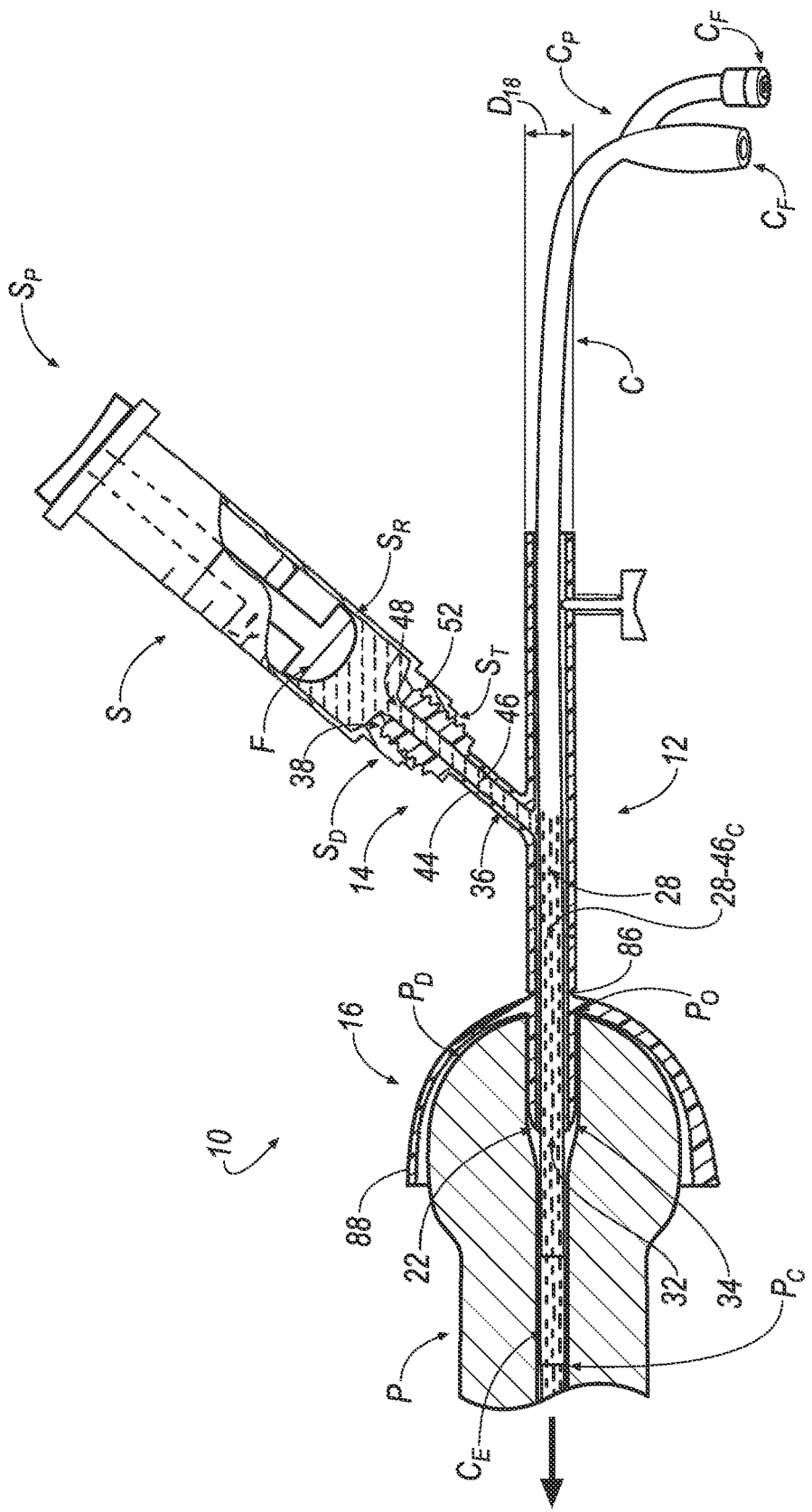

The selective injection of the fluid, F, as described above in advance of the distal end, $C_D$, of the catheter, C, serves two functions. First, the fluid, F, has the benefit of distending and increasing the diameter of the urethra, $P_C$, (as a result of filling the urethra, $P_C$, with the fluid, F) as well as smoothing and straightening out the curves and bends resulting from the natural tortuosity of the patient's urethra, $P_C$. This distending of the urethra, $P_C$, improves the ease and efficiency with which the catheter, C, can be inserted into the urethra, $P_C$. Additionally, the presence of the fluid, F, along the entire course of the urethra, $P_C$, helps to reduce the wall-to-wall friction between the catheter, C, and urethra, $P_C$, thereby further improving catheter insertion efficiency. Furthermore, once the distal end 22 of the tube-shaped body 18 of the first conduit 12 is placed within the a portion of the urethra, $P_C$, proximate the meatus, $P_O$, the rigidity of the distal end 22 of the tube-shaped body 18 of the first conduit 12 provides the benefit of preventing iatrogenic urethral compression and friction as a result of the operator grasping the patient's penis, P. Further, an additional benefit is that the extra-urethral portion of the catheter, C, that is arranged outside of the passage 28 of the catheter guide, 10, near the proximate end 20 of the catheter guide 10 remains free of fluid, F, during the insertion of the catheter, C, into the urethra, $P_C$, which thereby improves the transfer force from the user's hand to the catheter, C, which translates into improved speed and efficiency with which the catheter, C, can be placed. Thus, as seen in FIGS. 6D-6E, as a result of the fluid, F, coating the distal end, $C_D$, of the catheter, C, and the urethra, $P_C$, the catheter guide 10 contains and controls the fluid, F, as the distal end, $C_D$, of the catheter, C, is guided out of the distal end 22 of the tube-shaped body 18 of the first conduit 12 and through the meatus, $P_O$, of the penis, P, and into the urethra, $P_C$, of the penis, P, for subsequent arrangement within the urinary bladder of the patient.

Figure 6F:
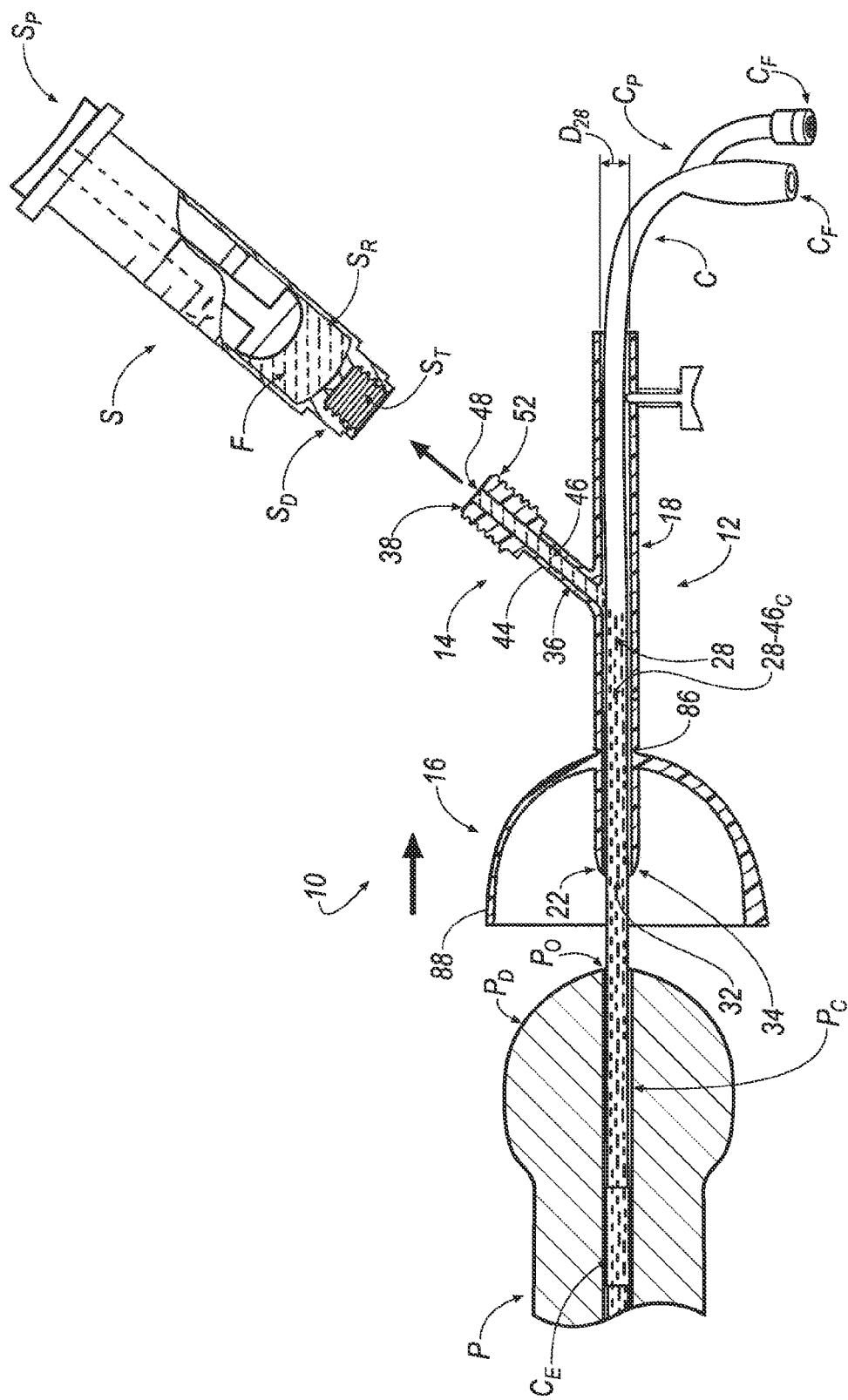
Figure 6G:
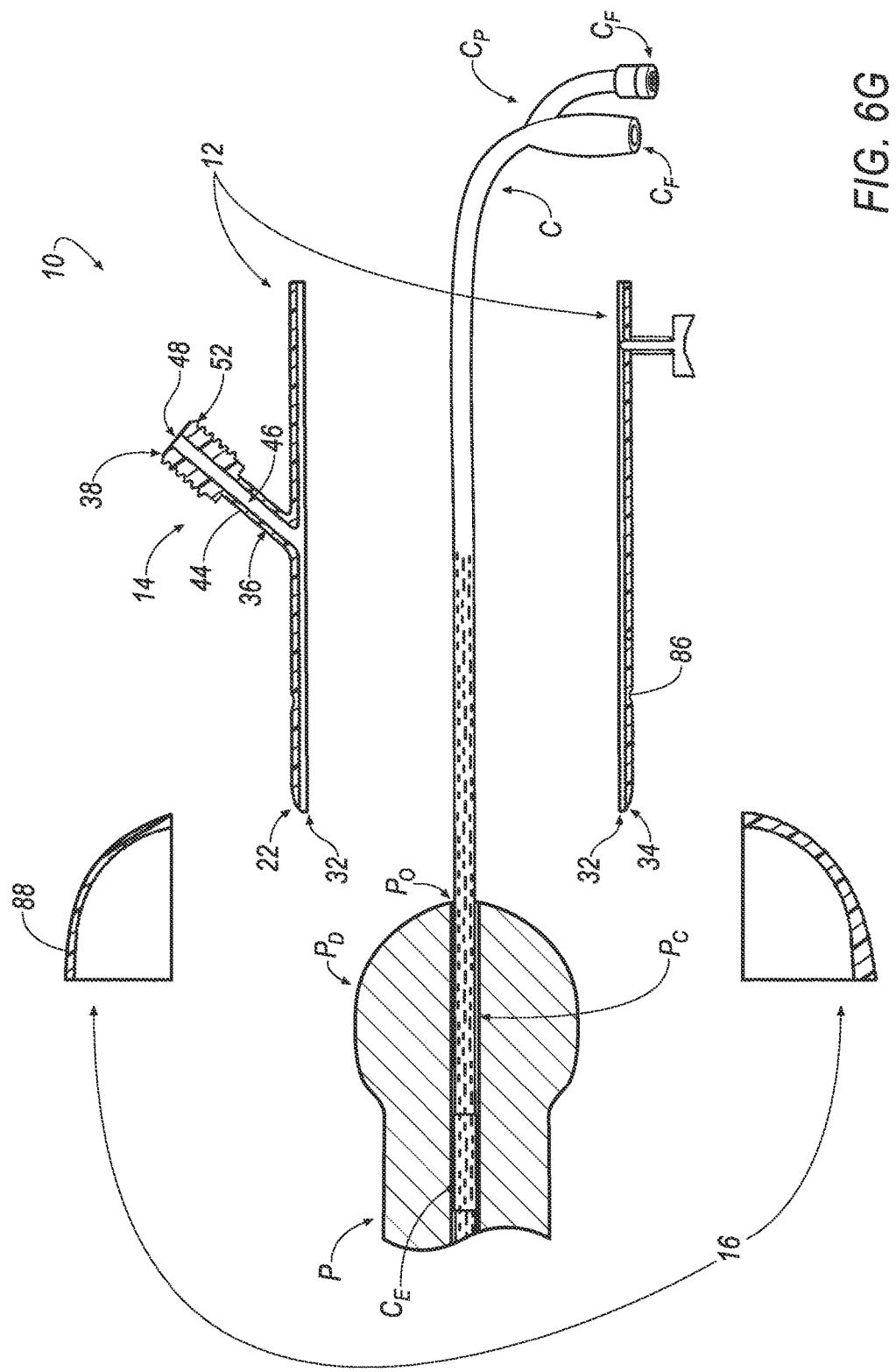

Referring to FIG. 6F, once the catheter, C, is arranged within the urinary bladder of the patient, the user (e.g., a nurse) may selectively remove the syringe, S, from the catheter guide 10. Subsequently, the user may remove the shield member 16 of the catheter guide 10 from being arranged about the glands penis, $P_D$, of the penis, P, such that the glands penis, $P_D$, of the penis, P, is no longer disposed within the glands penis-receiving cavity 72 of the shield member 16. Additionally, after removing the shield member 16 of the catheter guide 10 from being arranged about the glands penis, $P_D$, of the penis, P, any fluid, F, that may migrate out of the passage 28 formed by the tube-shaped body 18 of the first conduit 12 at the opening 32 formed in the distal end 22 of the tube-shaped body 18 of the first conduit 12 may be contained by the concave side 68 of the shield member 16 such that the fluid, F, is inhibited from randomly migrating in a plurality of directions about one or more of the patient and the user.

As seen in FIG. 6F, after selectively removing the catheter guide 10 from being arranged about the glands penis, $P_D$, of the penis, P, the catheter, C, remains arranged within the passage 28 of the first conduit 12 of the catheter guide 10. Although the catheter guide 10 is withdrawn from the glands penis, $P_D$, of the penis, P, the user (e.g., the nurse) is unable to selectively axially withdrawal the catheter guide 10 from the catheter, C, due interference arising from the one or more fluid interface ports, $C_F$, which have a larger diameter than that of the diameter, $D_{28}$, of the passage 28 of the first conduit 28. As such, with reference to FIG. 6G, the user may exploit the one or more weakened zones 84, 86, 88 of the catheter guide 10 in order to frangibly-break the catheter guide 10 to thereby radially remove the catheter guide 10 from the catheter, C. If, for example, the catheter guides 10', 10'', 10''', 10'''' were utilized for guiding the catheter, C, into the urinary bladder of the patient, the user may similarly deconstruct the catheter guide 10', 10'', 10''', 10'''' for example, by one or more of the following techniques: (1) removing the adapters 94', 96' and separating the catheter guide 10' into a first part 10a' and a second part 10b' (as seen in FIGS. 2A-2B), (2) exploiting the one or more weakened zones 84a", 84b", 84c", 86", 88" (as seen in FIGS. 3A-3C), (3) removing the adapter 96''', decoupling the shield member 16''' from the first guide 12''' and exploiting the one or more weakened zone 84'''(as seen in FIG. 4), and (4) exploiting the one or more weakened zones 86'''', 88'''' (as seen in FIG. 5).

Referring to FIG. 7, an exemplary kit, K, is shown. The kit, K, may include at least a catheter, C, and any of the catheter guides 10, 10', 10", 10''', 10'''' described above. In some examples, the kit, K, may include a syringe, S, which may contain the fluid, F. The kit, K, may also include a bag, B, that contains two or more of the following: the catheter, C, the catheter guide 10, 10', 10", 10''', 10'''' and the syringe, S. Although not illustrated, the kit, K, may include one or more items such as, for example: an inflator (not shown) that interfaces with the catheter, C, for inflating the expandable member, $C_E$, one or more disinfecting wipes (not shown) for disinfecting the glands penis, $P_D$, of the penis, P, or the like.

As a person skilled in the art will readily appreciate, the above description is meant as an illustration of implementation of the principles disclosed herein. This description is not intended to limit the scope or application of this disclosure in that device and method disclosed are susceptible to modification, variation, and change, without departing from spirit of this disclosure, as defined in the following claims.

What is claimed is:

1. A catheter guide comprising:
    a first conduit for guiding a catheter, wherein the first conduit includes a tube-shaped body having a proximal end and a distal end, and wherein the distal end of the tube-shaped body is sized and configured to be inserted into a urethra;
    a second conduit connected to an outer surface of the first conduit, wherein a passage extending through the first conduit is fluidly-connected to a passage extending through the second conduit;
    a shield member, wherein the shield member includes an inner surface and an outer surface, wherein the shield member is connected to the outer surface of the first conduit, and wherein the distal end of the tube-shaped body of the first conduit extends through the shield member and beyond at least part of the inner surface of the shield member;
    a grasping member that extends radially outwardly from and is integrally connected to the outer surface of the first conduit, wherein the grasping member is angularly offset from the second conduit at a first angle; and
    a third conduit connected to the outer surface of the first conduit, wherein the passage extending through the first conduit is fluidly-connected to a passage extending through the third conduit, wherein the grasping member is angularly offset from the third conduit at a second angle, and wherein the second conduit is angularly offset from the third conduit at a third angle,
    wherein the first conduit of the catheter guide includes one or more weakened zones, wherein at least one first weakened zone of the one or more weakened zones longitudinally extends along the length of the first conduit.

2. The catheter guide according to claim 1, wherein a first weakened zone of the at least one first weakened zone of the one or more weakened zones longitudinally extends along the length of the first conduit between the second conduit and the grasping member, wherein
a second weakened zone of the at least one first weakened zone of the one or more weakened zones longitudinally extends along the length of the first conduit between the grasping member and the third conduit, and wherein
a third weakened zone of the at least one first weakened zones of the one or more weakened zones longitudinally extends along the length of the first conduit between the second conduit and the third conduit.

3. The catheter guide according to claim 1, wherein a first portion of the second conduit is arranged exterior of a glands penis-receiving cavity of the shield member, wherein a second portion of the second conduit extends through a passage formed in the shield member, and wherein a third portion of the second conduit is arranged within the glands penis-receiving cavity of the shield member where the second conduit extends from the outer surface of the first conduit.

4. A method for utilizing the catheter guide of claim 1, comprising the steps of:
    inserting a portion of the distal end of the tube-shaped body of the first conduit into a meatus of the penis;
    extending the at least a portion of the distal end of the tube-shaped body of the first conduit into a urethra of the penis for arranging the passage extending through the first conduit in fluid communication with the urethra of the penis;
    connecting a syringe including a fluid to the second conduit;
    arranging a distal end of a catheter within the passage extending through the first conduit for forming a fluid sub-chamber defined by all of the passage extending through the second conduit and a portion of the passage extending through the first conduit;
    expelling a portion of the fluid from the syringe into the fluid sub-chamber for guiding the fluid directly into the urethra of the penis for distending the urethra of the penis;
    advancing the distal end of a catheter out of an opening formed in the distal end of the first conduit for advancing the distal end of a catheter into the urethra of the penis that is distended by the fluid;
    removing the catheter guide from being arranged about the glands penis of the penis while the catheter remains within the urethra; and
    separating the catheter guide into two or more pieces for radially removing the catheter guide from being arranged about the catheter,
    wherein the separating step further includes firstly circumferentially separating the shield member from the first conduit and then secondly longitudinally separating the first conduit into two or more pieces for radially removing the first conduit from being arranged about the catheter.

5. A method for utilizing the catheter guide of claim 1, comprising the steps of:
    inserting a portion of-the distal end of the tube-shaped body of the first conduit into a meatus of the penis;
    extending the at least a portion of the-distal end of the tube-shaped body of the first conduit into a urethra of the penis for arranging the passage extending through the first conduit in fluid communication with the urethra of the penis;
    connecting a syringe including a fluid to the second conduit;

arranging a distal end of a catheter within the passage extending through the first conduit for forming a fluid sub-chamber defined by all of the passage extending through the second conduit and a portion of the passage extending through the first conduit;

expelling a portion of the fluid from the syringe into the fluid sub-chamber for guiding the fluid directly into the urethra of the penis for distending the urethra of the penis;

advancing the distal end of a catheter out of an opening formed in the distal end of the first conduit for advancing the distal end of a catheter into the urethra of the penis that is distended by the fluid;

removing the catheter guide from being arranged about the glands penis of the penis while the catheter remains within the urethra; and separating the catheter guide into two or more pieces for radially removing the catheter guide from being arranged about the catheter, wherein the separating step includes firstly longitudinally separating the shield member into two or more pieces for radially removing the shield member from the first conduit and then secondly longitudinally separating the first conduit into two or more pieces for radially removing the first conduit from being arranged about the catheter.

6. A catheter guide comprising:
a first conduit for guiding a catheter, wherein the first conduit includes a tube-shaped body having a proximal end and a distal end, and wherein the distal end of the tube-shaped body is sized and configured to be inserted into a urethra;

a second conduit connected to an outer surface of the first conduit, wherein a passage extending through the first conduit is fluidly-connected to a passage extending through the second conduit;

a shield member, wherein the shield member includes an inner surface and an outer surface, wherein the shield member is connected to the outer surface of the first conduit, and wherein the distal end of the tube-shaped body of the first conduit extends through the shield member and beyond at least part of the inner surface of the shield member; and one or more adapters that selectively-retain a first part of the catheter guide to a second part of the catheter guide, wherein a distal end adapter of the one or more adapters is arranged about the outer surface of the first conduit near a region where the shield member is connected to the outer surface of the first conduit, and wherein one or more longitudinal seams longitudinally splits the catheter guide into the first part and the second part.

* * * * *